(12) United States Patent
Novek

(10) Patent No.: US 10,233,089 B2
(45) Date of Patent: *Mar. 19, 2019

(54) INTEGRATED PROCESS FOR CARBON CAPTURE AND ENERGY PRODUCTION

(71) Applicant: Ethan Novek, Greenwich, CT (US)

(72) Inventor: Ethan Novek, Greenwich, CT (US)

( * ) Notice: Subject to any disclaimer, the term of this patent is extended or adjusted under 35 U.S.C. 154(b) by 174 days.

This patent is subject to a terminal disclaimer.

(21) Appl. No.: 15/476,494

(22) Filed: Mar. 31, 2017

(65) Prior Publication Data

US 2017/0267539 A1 Sep. 21, 2017

Related U.S. Application Data

(63) Continuation of application No. 14/826,771, filed on Aug. 14, 2015, now Pat. No. 9,624,111.

(60) Provisional application No. 62/106,822, filed on Jan. 23, 2015, provisional application No. 62/090,272, (Continued)

(51) Int. Cl.
| | | |
|---|---|---|
| *C07C 269/08* | (2006.01) | |
| *C07C 269/00* | (2006.01) | |
| *C01C 1/02* | (2006.01) | |
| *C07C 1/26* | (2006.01) | |
| *C01B 21/12* | (2006.01) | |
| *C01B 32/50* | (2017.01) | |
| *C01B 32/60* | (2017.01) | |
| *C01C 1/26* | (2006.01) | |
| *C07C 269/06* | (2006.01) | |
| *C07C 273/10* | (2006.01) | |
| *H02K 7/18* | (2006.01) | |
| *C07C 273/04* | (2006.01) | |
| *B01D 53/62* | (2006.01) | |
| *B01D 61/06* | (2006.01) | |

(Continued)

(52) U.S. Cl.
CPC .............. *C01C 1/26* (2013.01); *B01D 53/62* (2013.01); *B01D 61/06* (2013.01); *C01B 32/50* (2017.08); *C07C 269/00* (2013.01); *C07C 269/06* (2013.01); *C07C 273/04* (2013.01); *C07C 273/10* (2013.01); *H02K 7/1823* (2013.01); *B01D 53/343* (2013.01); *B01D 53/58* (2013.01); *B01D 2251/206* (2013.01); *B01D 2251/60* (2013.01); *B01D 2251/606* (2013.01); *B01D 2252/10* (2013.01); *B01D 2252/202* (2013.01); *B01D 2252/205* (2013.01); *B01D 2257/406* (2013.01); *B01D 2257/504* (2013.01); *B01D 2258/0283* (2013.01); *Y02P 20/125* (2015.11); *Y02P 20/129* (2015.11)

(58) Field of Classification Search
None
See application file for complete search history.

(56) References Cited

U.S. PATENT DOCUMENTS

2011/0100218 A1\* 5/2011 Wolfe ................ B01D 53/1493
95/205
2014/0158616 A1\* 6/2014 Govind ................ C02F 1/5272
210/636

\* cited by examiner

*Primary Examiner* — Daniel Berns
(74) *Attorney, Agent, or Firm* — Gregory L. Porter; Hunton Andrews Kurth LLP

(57) ABSTRACT

The present invention pertains to new methods for generating energy and useful nitrogen compounds from captured carbon dioxide. It involves employing an osmotic engine, draw solution, and feed solution. An osmotic gradient between the solutions assists in generating energy and a solution of ammonium carbonate, ammonium bicarbonate or mixture thereof. This solution may be decomposed to form ammonia, carbon dioxide, a precipitate, or a mixture thereof.

20 Claims, 14 Drawing Sheets

Related U.S. Application Data filed on Dec. 10, 2014, provisional application No. 62/159,481, filed on May 11, 2015.

(51) Int. Cl.
*B01D 53/34* (2006.01)
*B01D 53/58* (2006.01)

INTEGRATED PROCESS FOR CARBON CAPTURE AND ENERGY PRODUCTION

CROSS-REFERENCE TO RELATED APPLICATIONS

This application is a continuation of U.S. Ser. No. 14/826,771 filed Aug. 14, 2015 which will issue as U.S. Pat. No. 9,624,111 which application claims priority to U.S. provisional patent application 62/090,272 filed Dec. 10, 2014; U.S. provisional patent application 62/106,822 filed Jan. 23, 2015; and U.S. provisional patent application 62/159,481, filed May 11, 2015, each of which is incorporated by reference herein in its entirety.

FIELD OF THE INVENTION

The inventions relate to methods and systems to generate electricity and/or useful compounds from captured carbon dioxide.

BACKGROUND AND SUMMARY OF THE INVENTION

Climate change due to increasing amounts of greenhouse gases in Earth's atmosphere poses one of the greatest threats to mankind and world's ecosystems as a whole. Carbon dioxide ($CO_2$) is one of the most significant contributors to climate change, making up approximately 77% of the world's greenhouse gas emissions by some estimates. Many of the $CO_2$ emissions are due to, for example, combustion from power plants or other industrial facilities.

There have been numerous methods and systems developed in attempts to reduce and/or eliminate these emissions. Such methods include carbon capture and storage or sequestration. Such methods often rely on separating (i.e. capturing) $CO_2$ from, for example, combustion gas or other $CO_2$ sources. Unfortunately, in order to be effective the captured $CO_2$ must then be disposed as opposed to released to the environment. The disposal methods developed thus far are very inadequate. For example, one such disposal method employed is compression followed by, for example, delivery to an underground geological formation or other manner of containment. In another method carbon dioxide is captured by ammonia and used in a forward osmosis process with high temperature and pressure. Unfortunately, such current methods often require complex apparatuses, are expensive to implement, consume vast amounts of energy, and/or usually do not yield usable or saleable products.

It would therefore be desirable to determine new methods for reducing and/or eliminating $CO_2$ emissions. It would further be advantageous if such new methods could be implemented using less complex equipment, were cost-effective, consumed less energy, and/or yielded usable or saleable products. Advantageously, the instant processes accomplish one or more up to all of the aforementioned.

In one embodiment the invention pertains to an integrated process for generating energy and useful nitrogen compounds from captured carbon dioxide. The process comprises forming a solution of ammonium carbonate, ammonium bicarbonate, ammonium carbamate or mixture thereof. The solution is formed from at least a portion of captured carbon dioxide. The solution of ammonium carbonate, ammonium bicarbonate, ammonium carbamate or mixture thereof is decomposed to form ammonia, carbon dioxide, a precipitate, or a mixture thereof. The decomposing of the solution is further characterized by one or more of the following:

(a) decomposing such that ammonia and carbon dioxide are formed in a molar ratio suitable for production of ammonium carbamate, urea, or a derivative thereof;
(b) decomposing at about atmospheric pressure;
(c) decomposing in the substantial absence of high temperature equilibrium;
(d) decomposing using low grade heat;
(e) decomposing in the presence of a semipermeable membrane, condensing, or a water soluble, solvent under suitable conditions to form substantially separated ammonia and carbon dioxide; or
(f) decomposing under conditions to form a precipitate comprising a salt of carbonate, bicarbonate, carbamate, or a mixture thereof.

In another embodiment the integrated process may comprise employing an osmotic engine. The osmotic engine comprises: (1) the formed solution of ammonium carbonate, ammonium bicarbonate, ammonium carbamate or mixture thereof as a draw solution and (2) a feed solution having a lower osmotic pressure than said draw solution to generate a gradient. The gradient may be used to generate energy and a second solution of ammonium carbonate, ammonium bicarbonate, ammonium carbamate or mixture thereof wherein said second solution has a lower osmotic pressure than the draw solution and wherein at least a portion of said second solution is subjected to decomposing as described above.

In another embodiment the invention pertains to an integrated process for generating energy and useful nitrogen compounds from captured carbon dioxide comprising capturing carbon dioxide from a combustion emission stream by exposing the carbon dioxide to aqueous ammonia under conditions suitable to form a draw solution comprising ammonium carbonate, ammonium bicarbonate, ammonium carbamate, or mixture thereof. An osmotic engine is employed comprising: (1) the draw solution and (2) a feed solution having a lower osmotic pressure than said draw solution to generate a gradient. The gradient is used to generate energy and a second solution of ammonium carbonate, ammonium bicarbonate, ammonium carbamate, or mixture thereof wherein said second solution has a lower osmotic pressure than the draw solution. The second solution of ammonium carbonate, ammonium bicarbonate or mixture thereof may be decomposed to form ammonia, carbon dioxide, or a mixture thereof. The decomposing of the second solution is further characterized by one or more of the following:

(a) decomposing such that ammonia and carbon dioxide are formed in a molar ratio suitable for production of ammonium carbamate, urea, or a derivative thereof;
(b) decomposing at about atmospheric pressure;
(c) decomposing in the substantial absence of high temperature equilibrium;
(d) decomposing using low grade heat; or
(e) decomposing in the presence of a semipermeable membrane, cooling, or a water soluble solvent under suitable conditions to form substantially separated ammonia and carbon dioxide. The ammonia and carbon dioxide that were decomposed from the second solution may be reacted under conditions to form one or more useful products selected from the group consisting of ammonium carbamate, urea, or a derivative thereof.

In another embodiment the invention pertains to an integrated process for generating energy and useful nitrogen compounds from captured carbon dioxide comprising contacting ammonia, carbon dioxide or a solution made therefrom with a suitable draw solution. The contacting is conducted under conditions such that a precipitate is formed which comprises ammonia carbonate, ammonia bicarbonate, ammonia carbamate, or a mixture thereof. Suitable draw solutions may be selected from the group consisting of ammonium sulfate, ammonium nitrate, potassium carbonate, potassium bicarbonate, or a mixture thereof.

DETAILED DESCRIPTION

Figure 1:
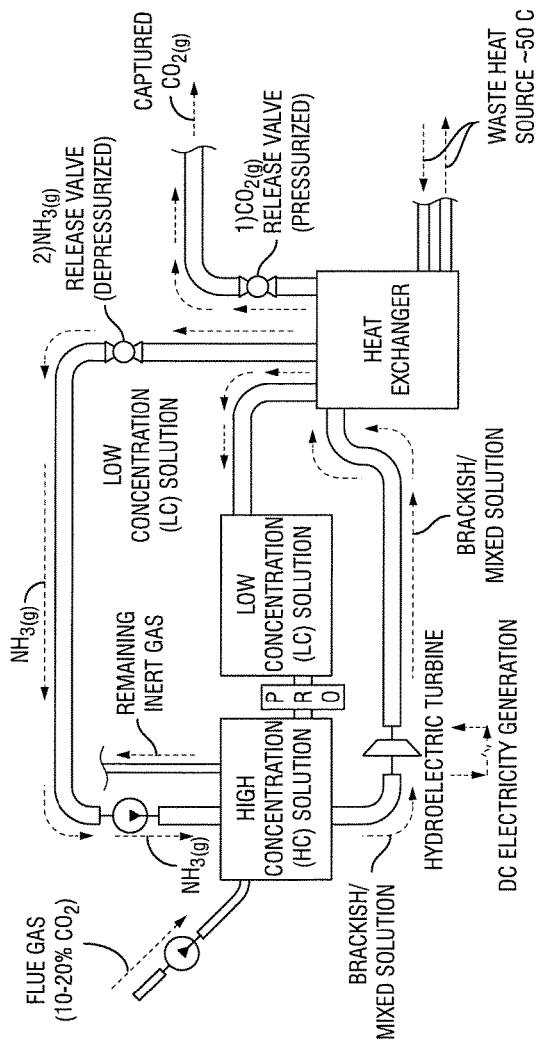
FIG. 1 illustrates an embodiment of Pressure Retarded Osmosis Waste Heat Recovery System with Carbon Capture using Pressurization and Depressurization.

The instant invention generally pertains to an integrated process for generating energy and useful nitrogen compounds from captured carbon dioxide. The source of the captured carbon dioxide is not particularly important and generally it may be from any useful source. Such sources include, but are not limited to, combustion or oxidation of one or more hydrocarbons, from steam reforming, from gas shift reaction, from catalytic reforming, from natural gas purification, from land fill gas, from biogas, from waste water treatment, fermentation, respiration, from air, or from mixtures thereof. Carbon dioxide from gas purification is typically from gas streams containing hydrogen, methane, or other desired gas by capturing carbon dioxide in these gas streams at a temperature of from about 50 to about 70° C.

Similarly, the method of capturing the carbon dioxide is not critical and may, of course, vary depending upon the source of the carbon dioxide, equipment available, desired purity, etc. In one embodiment carbon dioxide may be captured from the combustion or oxidation of one or more hydrocarbons in some convenient manner. For example, flue gas from a power plant of some sort may be subjected to, for example, ammonia, preferably aqueous ammonia, or other suitable substance such that the carbon dioxide is dissolved and therefore removed from the flue gas. In such a method it is not particularly critical when the carbon dioxide is captured so long as it is not released to the environment. Moreover, the flue gas may be further treated before or after being subjected to the aqueous ammonia depending upon the amounts and components of the starting flue gas and desired treated product.

The capturing of the carbon dioxide may be part of or separate from the instant integrated process. That is, carbon dioxide in flue gas or another source may be exposed to ammonia to form an aqueous solution of ammonium carbonate, ammonium carbamate, ammonium bicarbonate or mixture thereof for direct use in and as part of the present processes. Generally, when water, carbon dioxide, and ammonia are reacted an aqueous mixture of ammonium carbonate, ammonium bicarbonate, ammonium carbamate is formed. The amounts of each component depend on the relative amounts of starting ingredients and the other conditions but generally ammonium carbamate is often present in smaller amounts than ammonium carbonate or ammonium bicarbonate.

Carbon dioxide capturing has been described by, for example, the following publications which are incorporated by reference herein: Kozak F, Petig A, Morris E, Rhudy R, Thimsen D. Chilled Ammonia Process for $CO_2$ Capture, *Energy Procedia* 1 (2009): 1419-1426; Sherrick B, Hammond M, Spitznogle G, Muraskin D., Black S., and Cage M. CCS with Alstom's Chilled Ammonia Process at AEP's Mountaineer Plant.; Yeh, A. "Comparison of Ammonia and Monoethanolamine Solvents to Reduce $CO_2$ Greenhouse Gas Emissions," *The Science of the Total Environment* 228 2-3 (1999): 121-33.; and Yeh, James T., Henry W. Pennline, Kevin P. Resnik, and Kathy Rygle. "Absorption and Regeneration Studies for $CO_2$." *Proceedings of Third Annual Conference on Carbon Capture & Sequestration*, Alexandria, Va. U.S. DOE—NETL and Parson Project Services, Inc., 6 Jun. 2004. Web. 13 Nov. 2010.

In another embodiment, captured carbon dioxide may be used to form a precipitate comprising ammonia carbonate, ammonia bicarbonate, ammonia carbamate, or a mixture thereof. The precipitate can then be used to form a draw solution for the osmotic engines described below. The precipitate may be formed in any convenient manner.

In one embodiment ammonia and carbon dioxide are contacted with a suitable draw solution under conditions such that a precipitate is formed. Alternatively, an aqueous solution made from ammonia and carbon dioxide may be contacted with the suitable draw solution under conditions such that a precipitate is formed. In either case the carbon dioxide can be from any source including flue gas and other sources previously mentioned. Advantageously, the resulting precipitate generally comprises ammonia carbonate, ammonia bicarbonate, ammonia carbamate, or a mixture thereof. In this manner it may be mixed with appropriate aqueous solutions and used as a draw solution in the osmotic engines described below.

Suitable draw solutions for contacting with the ammonia and carbon dioxide (or a solution made therefrom) to form a precipitate will vary depending upon the application. Generally it may often be useful to employ a draw solution with a common ion as the desired precipitate (e.g., ammonium, carbonate, bicarbonate, carbamate). In this manner the presence of the common ion salt with a more soluble common ion will cause the lower solubility compound, e.g., ammonium bicarbonate, to precipitate. Such suitable draw solutions thus include, for example, ammonium sulfate, ammonium nitrate, potassium carbonate, potassium bicarbonate, or a mixture thereof. If desired, the precipitate may be filtered before using it further.

As an alternative to capturing as part of the instant process, an aqueous solution or precipitate of ammonium carbonate, ammonium bicarbonate or mixture thereof made from captured carbon dioxide may be acquired in any convenient manner for use in the present process. In any event, the purity and amounts of carbon dioxide, ammonia, and other ingredients employed is not particularly important so long as a suitable aqueous solution or precipitate of ammonium carbonate, ammonium bicarbonate or mixture thereof is formed. In some cases it may be desirable to subject the aqueous solution of ammonium carbonate, ammonium bicarbonate, ammonium carbamate or mixture thereof to further purification or treatment in order to make it suitable as a draw solution. For example, further amounts of carbon dioxide or ammonia may be added to make a desired concentration.

Osmotic Engine

The instant process may involve employing an osmotic engine or system. An osmotic engine as used herein is any system wherein an osmotic gradient between one or more draw solutions and one or more feed solutions may be employed to generate energy, one or more useful solutions or precipitates, or some combination thereof. An osmotic gradient may be generated in any convenient manner. For example, differences in salt concentrations may commonly result in useful osmotic gradients.

Specific useful types of osmotic engine systems and other systems that generate electricity from osmotic or concentration gradients may include, for example, pressure retarded osmosis, reverse electrodialysis, capacitive mixing power production using components including nano battery electrodes, ultra capacitors, or combinations thereof. Among other useful references such systems are described in, for example, *Energy Procedia*, Volume 20, 2012, Pages 108-115 Technoport 2012—Sharing Possibilities and 2nd Renewable Energy Research Conference (RERC2012) CAPMIX—Deploying Capacitors for Salt Gradient Power Extraction; M. F. M. Bijmans, et al. which is incorporated herein by reference. Osmotic heat engines are capable of generating electricity from low grade heat, which can be from various waste heat sources (e.g. power plant) or renewable sources, for example, solar photovoltaic waste heat, solar thermal or geothermal energy.

The osmotic engine system may be an open or closed system and may be a continuous or batch process depending upon the starting materials, desired products, and equipment. If employing a closed system, then it may be desirable to have one or more valves or other gas release mechanisms. In this manner headspace gas such as, for example, carbon dioxide may be released while the system is kept at a desired pressure. In some cases it may be desirable to actively pressurize the system such that ammonia stays in aqueous solution while carbon dioxide is in the overhead space. In such a case one or more gas turbines may be used to keep the system pressurized and, if desired, generate electricity from the expansion of carbon dioxide gas. The system can be pressurized in any convenient manner. In one embodiment, carbon dioxide formed in the integrated process, e.g., from the decomposition of ammonium carbonate, ammonium bicarbonate, ammonium carbamate solution, may be used to pressurize the system. Additionally or alternatively, one or more other pumps or other devices may be employed.

While the above specifically described osmotic engines may be usefully employed, the invention will be further described by reference to a general osmotic engine system. The system can run carbon capture, electricity generation, and other related processes simultaneously, although different aspects of the system may be conducted at different time or rates.

General Osmotic Engine System

In this embodiment, water is transferred from the feed solution across one or more membranes. This transfer may be employed, if desired, to generate useful energy such as electricity. While the energy may be generated in any convenient manner, a hydroelectric generator may be particularly useful. Regardless of whether a hydroelectric generator is employed one or more draw solutions are employed. The draw solution usually comprises ammonium carbonate, ammonium carbamate, ammonium bicarbonate or mixture thereof formed from at least a portion of captured carbon dioxide as described above.

Pressure retarded osmosis systems usually separate one or more draw solutions from one or more feed solutions using one or more membranes. The system may be open to the atmosphere, closed, or partially closed depending upon the specific equipment, solutions, and membrane employed as well as, the desired results. The draw and feed solution(s) usually have an osmotic pressure differential, i.e., gradient, such that feed solution from a feed solution chamber is drawn into the draw solution in a draw solution chamber through the one or more membranes. In this manner, useful kinetic energy may be generated. Such energy may be used to, for example, spin a turbine or in some other useful manner. The amount of energy generated is, of course, related to the size of equipment and amount of solutions. However, generally the amount may be proportional to the differences in osmotic pressure between the draw and feed solutions.

The type of membrane employed is not particularly critical so long as it functions to allow the passage of certain substances, e.g., water, while preventing the passage of others, e.g., salts. Such semipermeable membranes are known in the art and include, for example, a thin-film composite (TFC) membrane. Such membranes may be made of any convenient substance. In one embodiment the membrane is comprised of a selective polyamide layer with a support such as polysulfone. Suitable membranes are described in, for example, Yip et al., *Environ. Sci. Technol.*, 2011, 45 (10), pp 4360-4369 which is incorporated herein by reference.

In one example, if a draw solution comprising ammonium carbonate, ammonium bicarbonate, ammonium carbamate or mixture thereof and one or more appropriate membranes (pressure retarded or otherwise) are employed with a feed solution of lower osmotic pressure, then typically useful energy is generated.

The feed solution may be any useful solution so long as it has a suitably lower osmotic pressure such that under appropriate conditions it is capable of migrating across the membrane to the draw solution. The degree of osmotic pressure differential or gradient may vary depending upon the equipment, membrane, solutions, and desired results. Generally, for many systems a gradient may be generated using at least about 2M, or at least about 3M, or at least about 4M draw solution with, for example, a regenerated deionized feed solution. Useful systems may also use a feed solution comprising dissolved substances in such cases forward osmosis membranes may be employed and the osmotic pressure of the draw solution should greatly exceed the osmotic pressure of the feed solution. Accordingly, useful feed solutions include aqueous solutions such as deionized water or salt solutions such as, for example, seawater. In some cases at least a portion of the feed solution employed may be selected from the group consisting of seawater, produced water, or wastewater.

In addition to forming kinetic energy due to the gradient, a second solution is usually formed in the draw solution chamber. The second solution, like the draw solution, comprises ammonium carbonate, ammonium bicarbonate, ammonium carbamate or mixture thereof. However, this second solution differs from the original draw solution in that it usually has a lower osmotic pressure than the original draw solution. This is generally due to water being drawn across the membrane until the osmotic pressures are substantially equal in the draw solution and feed solution chambers due to the changes in salt concentrations. Therefore, in most instances the remainder of the feed solution will comprise a higher osmotic pressure than the starting feed solution due to the migration of the water to the draw solution chamber.

Decomposition of the Solution

Typically, the second solution of ammonium carbonate, ammonium bicarbonate, ammonium carbamate, or mixture thereof is decomposed to form ammonia, carbon dioxide, a precipitate, or a mixture thereof. The specific manner of decomposition will vary depending upon the concentrations, other ingredients, and desired products and form, e.g., solution or gas. That is, advantageously decomposition of the second solution may be tailored depending upon whether it is desired to separate ammonia and carbon dioxide, as well as whether gaseous or aqueous substances are desired. If a gaseous mixture of ammonia and carbon dioxide is formed and separation is desired then a gas separation membrane or fractional distillation may be subsequently employed.

Advantageously the decomposition may be conducted under relatively moderate conditions that do not employ large amounts of energy. Moreover, the decomposition may be conducted such that desirable molar ratios of carbon dioxide to ammonia are obtained. Such molar ratios may be very suitable for making urea, ammonium carbamate and other useful products.

Typically, the decomposing of the second concentrated solution is characterized by one, or two, or three, or four, or five, or more of the following: (a) decomposing such that ammonia and carbon dioxide are formed in a molar ratio suitable for production of ammonium carbamate, urea, or a derivative thereof; (b) decomposing at about atmospheric pressure; (c) decomposing in the substantial absence of high temperature equilibrium; (d) decomposing using low grade heat; (e) decomposing in the presence of a semipermeable membrane, cooling, or a water soluble solvent under suitable conditions to form substantially separated ammonia and carbon dioxide; or (f) decomposing under conditions to form a precipitate comprising a salt of carbonate, bicarbonate, or a mixture thereof.

In one embodiment the decomposing of the second solution is characterized by decomposing such that ammonia and carbon dioxide are formed in a molar ratio such that subsequent processing may produce a suitable useful or saleable product. Such useful or saleable products include, for example, hydrocarbons as well as, compounds containing nitrogen such as ammonium carbamate, urea, or a derivative thereof such as cyanuric acid. In one embodiment the molar ratio may be controlled such that the molar ratio of ammonia to carbon dioxide is from about 1:2 to about 3:1, or from about 1.5:1 to about 1:1.5, or from about 1.25:1 to about 1:1.25, or even about 1:1. These molar ratio conditions can be extremely suitable for producing urea and its derivatives in further processing steps. Moreover, as shown by the molar ratios above a large amount of captured carbon dioxide can be put to use to make a useful product as opposed to disposal in some manner.

In another embodiment the decomposing of the second solution is characterized by decomposing in the absence of high temperature, the absence of high pressure, or the absence of both. Specific temperatures and pressures will vary depending upon the composition and the equipment as well as, the desired further products, if any. The decomposing of the second solution in this embodiment can generally be accomplished at a pressure of from about 0.75 atmospheres to about 1.25 atmospheres, or even at about 1 atmosphere in many circumstances. Similarly, a temperature of less than about 80° C., or less than about 70° C., or less than about 60° C., or less than about 55° C., or less than about 50° C., or less than about 45° C., or even as low as about 40° C. may be employed depending upon the pressure. In this manner low grade heat generated in this process or from another process may be employed. Suitable sources for such low grade heat include, for example, flue gas heat, power plant heated run-off water, Kalina cycles, organic rankine cycles, geothermal gradients, ocean depths, diurnal temperature variations, solar power, various other waste heat sources, etc. In this manner, heat that would otherwise go unused in many cases along with captured carbon dioxide that may otherwise be disposed may be employed in the process or other processes to generate electricity and useful compounds.

In another embodiment the decomposing of the second solution is characterized by decomposing in the presence of a semipermeable membrane such as gas separation membrane to form substantially separated ammonia and carbon dioxide. In this embodiment a semipermeable membrane is employed wherein one or the other, but not both, ammonia or carbon dioxide may migrate through the semipermeable membrane such that substantially separated ammonia and carbon dioxide is formed. Such semipermeable membranes are known in the art and include, for example, those described in, for example, Toy et al. "$CO_2$ Capture Membrane Process for Power Plant Flue Gas" Final Technical Report for Period of Performance: Oct. 1, 2008 to Sep. 30, 2011, published pursuant to DOE Cooperative Agreement No. DE-NT0005313 which paper is incorporated herein by reference.

In some instances, it may be useful to, for example, heat the second solution to its decomposition temperature, e.g., at least about 41° C. at standard pressure, in a sealed container separated by a semipermeable membrane from an aqueous third solution. The third solution may have a lower osmotic pressure than the second solution, e.g., water or water comprising salts such as NaCl. In this manner even though the second solution is heated above the decomposition temperature there is little to no decomposition gases formed because of the sealed container with a lack of headspace for formation. If, for example, carbon dioxide is then contacted with said third aqueous solution at a lower temperature than 41° C., then aqueous ammonia will, under suitable conditions, often migrate across said semipermeable membrane from said second solution to said third aqueous solution across the membrane. Current membranes sometimes have difficulty rejecting non-ionic ammonia species (e.g., $NH_{3\,(aq)}$) allowing them to migrate or diffuse in a similar manner to water. Said contacting with carbon dioxide may involve bubbling captured carbon dioxide or otherwise exposing carbon dioxide to the third aqueous solution. Advantageously, this may convert at least a portion of the third solution to one comprising ammonium carbonate, ammonium bicarbonate or mixture thereof. This solution or a portion of it may in turn be recycled for use as the draw solution for the osmotic engine. The second solution then comprises carbonic acid and when depressurized yields carbon dioxide gas suitable for any purpose and a solution which is suitable for use as a feed solution in the same or another osmotic engine.

Alternatively, instead of contacting carbon dioxide with third aqueous solution at a lower temperature than 41° C., the third solution may be heated or kept at substantially the same temperature as the second solution which is heated to at least about 41° C. In this manner, aqueous ammonia may be separated from the third solution via any convenient method such as membrane distillation.

In yet another embodiment, the decomposing of the second solution is characterized by decomposing in the presence of condensing, e.g., cooling. The conditions may be such that a substantial portion of the ammonia is condensed while a majority of the carbon dioxide is not condensed. In this manner, substantially separated ammonia and carbon dioxide are formed. Said condensing may be accomplished in any convenient manner. Suitable condensing includes, for example, cryogenic cooling, compression, etc.

In some instances it may be advantageous to decompose the second solution in the presence of a water-soluble, preferably non-azeotropic, solvent. Use of a non-azeotropic, solvent may facilitate the separation of solvents at a later time. Suitable solvents include those having a boiling point below that of water, e.g., acetone, methyl formate, ethanol, isopropyl alcohol, etc. In this manner under suitable conditions the solvent facilitates the release of carbon dioxide gas from the second solution and substantially separated ammonia and carbon dioxide may be formed. This is typically employed when the second solution has a less than or equal to 1M concentration of ammonium bicarbonate.

If desired, the decomposing of the second solution may be accomplished under conditions to form a precipitate which is then readily separable from the solution. Such precipitates include a salt of carbonate, carbamate, bicarbonate, or a mixture thereof. The specific manner of precipitate formation is not particularly important. In one embodiment a solvent is added to the second solution. This is typically employed when the second solution has a greater than or equal to 1M concentration of ammonium bicarbonate. In another embodiment a semipermeable membrane may be employed between the second solution and an aqueous third solution having a higher osmotic pressure, e.g., highly concentrated salt or other aqueous solution. In this manner, suitable precipitates, e.g., ammonium bicarbonate precipitate, are formed which may be removed in any convenient way such as by decanting, filtering, screening, or centrifuging. This is particularly effective when the second solution has a greater than or equal to 1M concentration of ammonium bicarbonate. The precipitate may then be employed in any useful manner such as making a further draw solution for the osmotic engine.

Use of Decomposed Second Solution

Generally, once separated the carbon dioxide and ammonia can be reused in the instant process or used elsewhere. For example, the ammonia may be employed to capture further carbon dioxide. The separated carbon dioxide gas may be used in, for example, enhanced oil recovery, disposed into saline aquifers, utilized in the accelerated weather of limestone process or used in other commercial or non-commercial application, including, but not limited to dry ice production. If desired, the ammonia and carbon dioxide may be employed to make a useful or salable product, e.g., ammonium carbamate which is useful to make urea which may be used to make cyanuric acid. Such procedures are described in, for example, Barzagli et al., Green Chem., 2011, 13, 1267-1274 which is incorporated herein by reference.

Use of Redox Battery

If desired a redox battery may be implemented into the process at a suitable place to generate electricity. Typically, the place where it is employed depends upon the specific system. Generally, if a redox battery is employed then it may be located across a heat exchanger. If a pressure retarded osmosis membrane is employed then a redox battery may be employed prior to or alternatively after such a membrane.

If employed, then the battery is typically selected from an ammonia, ammonium carbonate or ammonium bicarbonate redox battery. Such batteries will typically employ a suitable metal as the anode and the cathode. Such metals include, for example, copper, zinc, nickel, silver, lead, cobalt, and mixtures thereof. Copper may be particularly preferable for some applications. In this manner ammonia or ammonium may react with the metal at the anode to produce a water soluble complex cation. At the cathode the solution may be decomposed using, for example, low grade heat which causes a solid metal to deposit. DC electricity is generated by completing the circuit via connecting the electrodes with, for example, a wire. The electrodes may be periodically swapped to ensure the electrode in the oxidation solution does not become too depleted. Suitable batteries are described in, for example, *Energy Environ. Sci.*, 2015, 8, 343 Zhang et al., "A thermally regenerative ammonia-based battery for efficient harvesting of low-grade thermal energy as electrical power."

EXAMPLES OF SPECIFIC EMBODIMENTS

Example 1—Pressure Retarded Osmosis Waste Heat Recovery System with Carbon Capture Using Pressurization and Depressurization A specific embodiment of the instant invention is shown in FIG. 1. In this embodiment low grade heat is used to simultaneously capture carbon dioxide and generate electricity using osmotic gradients engineered using a heat exchange process. As shown, flue gas comprising carbon dioxide is contacted with ammonia to form the High Concentration Solution. The High Concentration Solution is used as a draw solution and comprises ammonium carbonate, ammonium bicarbonate or mixture thereof formed from at least a portion of captured carbon dioxide. The heat exchange process uses a pressurization and depressurization system, which pressurizes the system to release $CO_{2(g)}$ during carbon capture and depressurizes the system to release $NH_{3(g)}$ to recreate the high concentration draw solution.

Specifically, pressure retarded osmosis (PRO) and a thermolytic salt (e.g. ammonium bicarbonate or trimethylamine-carbon dioxide) are employed. The system can run the electricity generation, carbon capture and other related processes simultaneously, although different aspects of the system may be conducted at different time or rates. The system may also utilize reverse electrodialysis, nano battery electrodes, or ultra capacitors (CAPMIX) to generate electricity from concentration gradients in the electricity generation process.

The carbon capture process involves allowing the heat exchange region to pressurize during the heat exchange process. At a higher pressure, $NH_{3(g)}$ stays in solution, while the headspace contains mostly $CO_{2(g)}$. A valve or other gas release mechanism is opened from the container that allows headspace gas (mostly composed of $CO_{2(g)}$) to be released, while keeping the container pressurized. A gas turbine may be used to keep the system pressurized and generate electricity from the $CO_{2(g)}$ expansion. The system can be pressurized through the containment of the decomposition gases and/or through the use of a pump or other device to pressurize the system. The gas (mostly composed of $CO_{2(g)}$) is bubbled through water to remove traces of $NH_{3(g)}$ gas and is in a pure form. The $CO_{2(g)}$ is now ready for sale, storage, industrial chemical synthesis and/or other purposes.

After a significant amount of $CO_{2(g)}$ is released, the system is depressurized. The system can be depressurized through the release of decomposition/headspace gases and/or through the use of a pump, vacuum pump or other device to depressurize the system. The depressurization of the system allows for the release of $NH_{3(g)}$ from the solution, and a lower concentration of $CO_{2(g)}$. A gas stream mixture of a high concentration of $NH_{3(g)}$ and low concentration of $CO_{2(g)}$ is then recycled to recreate the HC solution through reaction with $CO_{2(g)}$ in a gas stream, including, although not limited to, flue gas, anaerobic digester gas, waste facility gas, ambient air or other treated or untreated $CO_{2(g)}$ containing gases.

Figure 2:
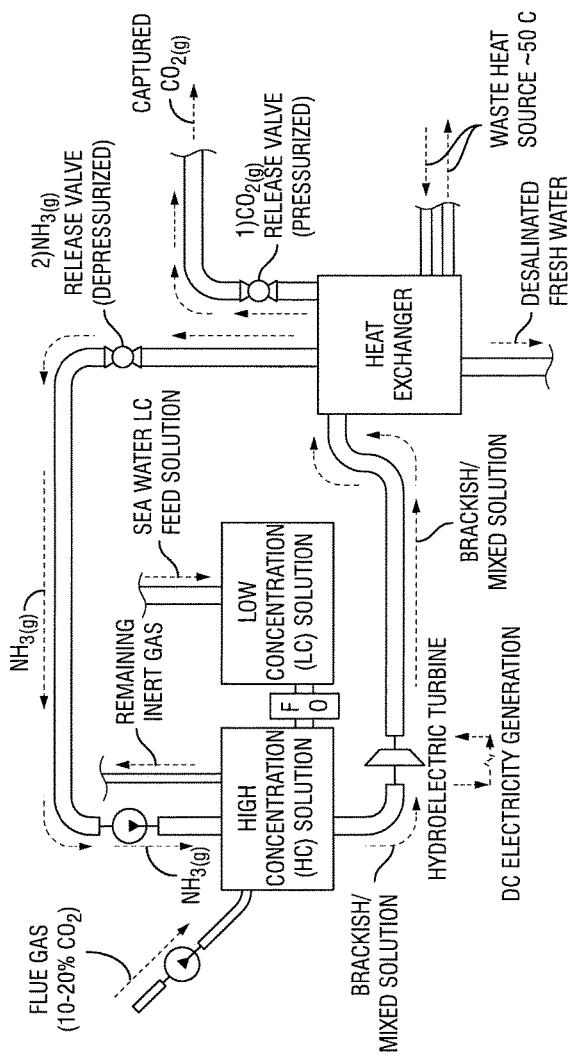
FIG. 2 illustrates an embodiment of Forward Osmosis Waste Heat Recovery System with Carbon Capture using Pressurization and Depressurization.

Example 2—Forward Osmosis Waste Heat Recovery System with Carbon Capture Using Pressurization and Depressurization Another specific embodiment of the instant invention is shown in FIG. 2. The system previously described above in Example 1 can be used as a forward osmosis water purification/desalination process that recovers heat in the system through electricity production, water desalination, and carbon capture. The system in Example 1 can be converted to a forward osmosis process by utilizing saline water (e.g. sea water or waste water) as the LC feed solution and sending desalinated water out of the system for sale or other purpose following the heat exchange process, rather than recycling the water to replenish the feed/LC solution. The system has all of the functionalities of the system in example 1 and desalinates water through forward osmosis.

Figure 3:
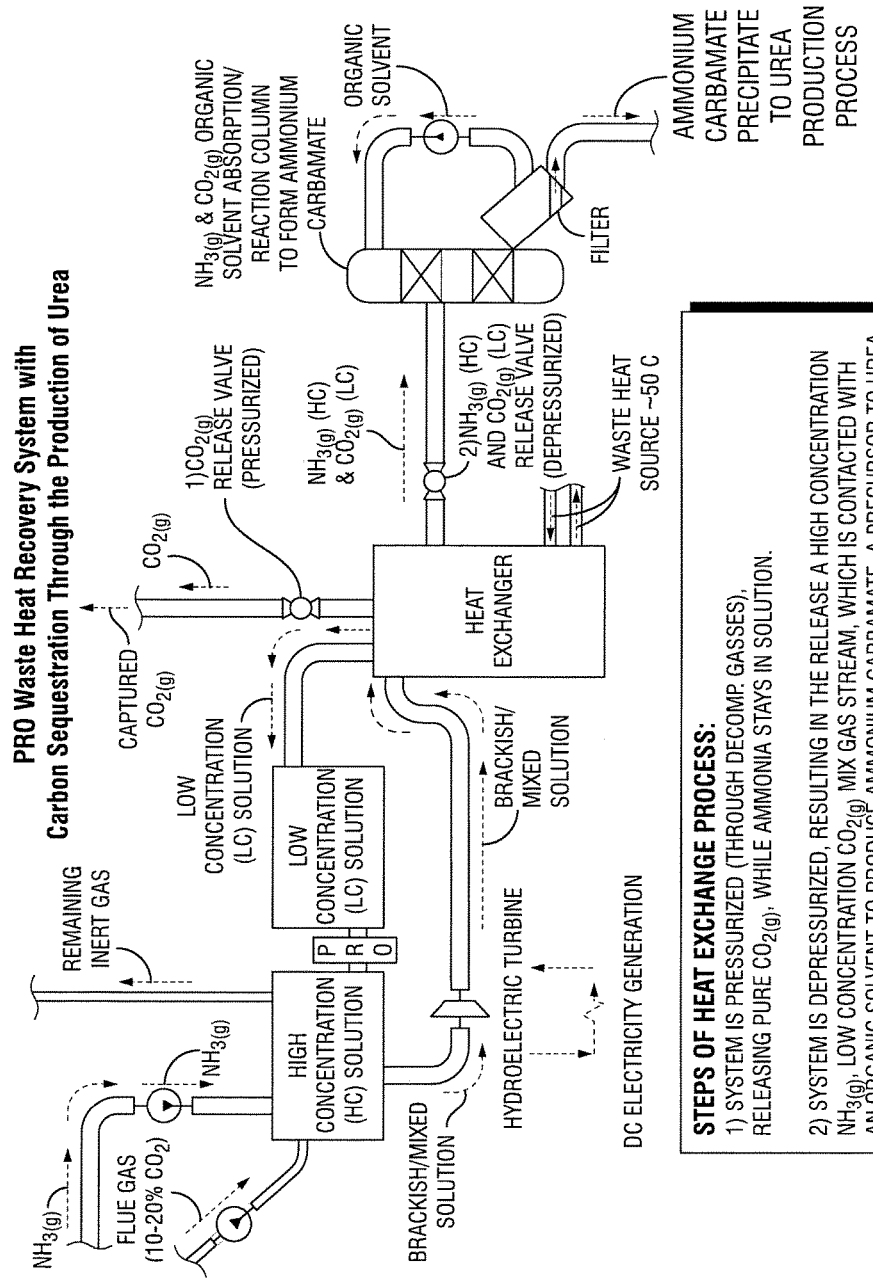
FIG. 3 illustrates an embodiment of Pressure Retarded Osmosis Waste Heat Recovery System with Carbon Sequestration through the Production of Urea.

Example 3—Pressure Retarded Osmosis Waste Heat Recovery System with Carbon Sequestration Through the Production of Urea Another specific embodiment of the instant invention is shown in FIG. 3. The system uses low grade heat to simultaneously generate electricity, and capture and sequester $CO_2$ in the form of ammonium carbamate, which is subsequently converted to urea. The pressurization and depressurization heat exchange process is employed to concentrate $NH_3$ and capture excess $CO_2$. The concentrated $NH_3$ and low concentration $CO_2$ gas stream created in the heat exchange process is contacted with an organic solvent to react and form ammonium carbamate.

The system continuously feeds $NH_{3(g)}$ and $CO_{2(g)}$ to recreate the HC draw solution in the electricity generation process. Therefore, in a version of the ammonium carbamate/urea production system, $NH_3$ is not recycled, although $NH_3$ may be recycled or recovered if desired. The concentrated $NH_3$ and lower concentration $CO_2$ (Note: the concentration of $CO_2$ could be equal to or greater in concentration than the $NH_3$, although a higher concentration of $NH_{3(g)}$ is preferred) gas stream is contacted with an organic solvent, which dissolves both $NH_3$ and $CO_2$, resulting in the gases reacting to form ammonium carbamate and/or a mixture comprising ammonium carbamate, ammonium carbonate and/or ammonium bicarbonate. The ammonium carbamate can be separated through precipitate removal methods, including, although not limited to, filter, screen, centrifuge, etc., and/or can be removed from solution through distillation of the solvent to remove dissolved ammonium carbamate.

If desired, the ammonium carbamate byproduct can be converted to urea via various processes, sold on its own, and/or converted into other compounds. The urea can also be converted into compounds that release $NH_3$ during synthesis, such as cyanuric acid, and/or compounds that absorb additional $CO_2$ during their synthesis. This could allow for additional $NH_3$ recovery/recycling and/or $CO_2$ sequestration.

Figure 4:
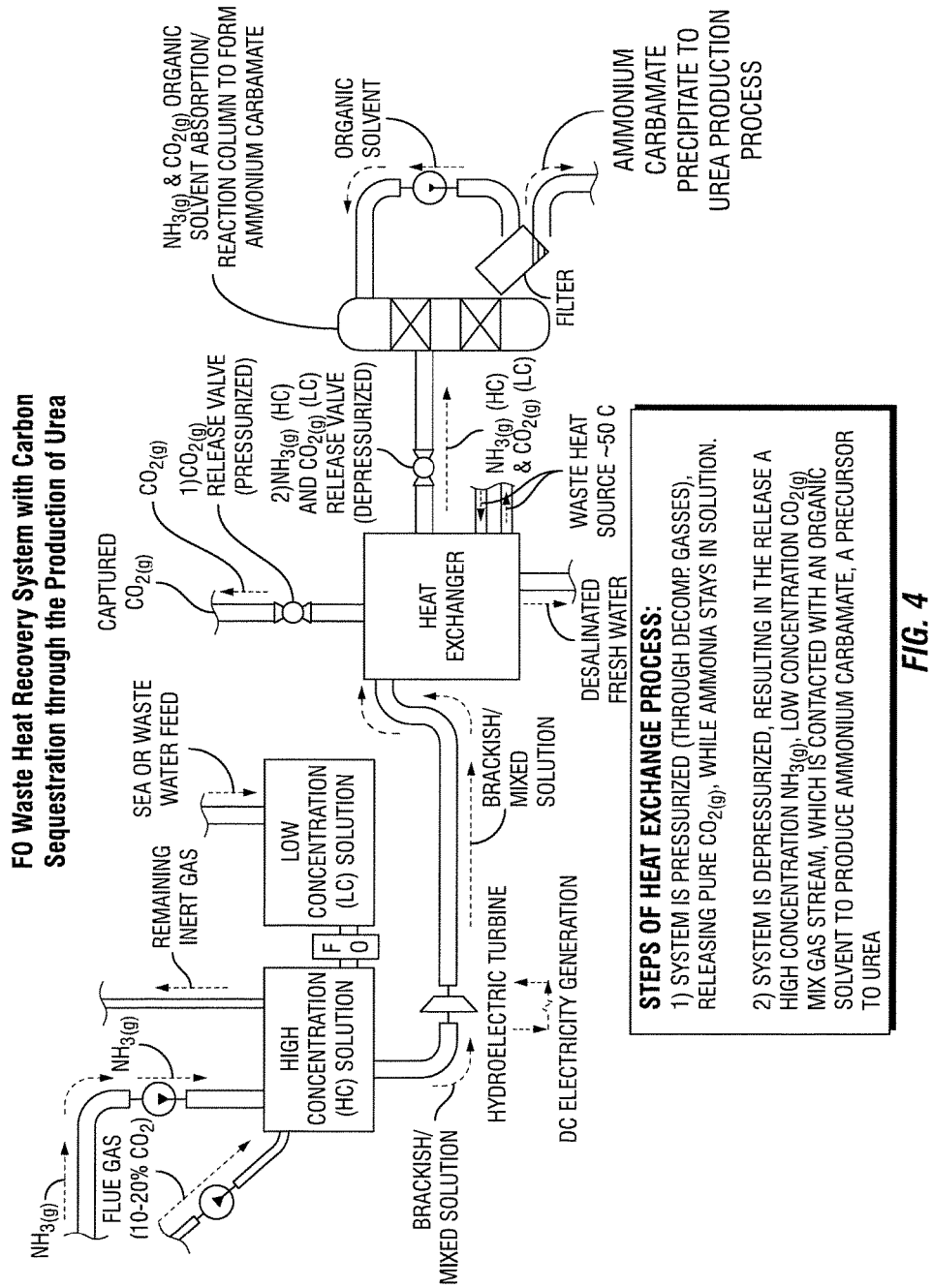
FIG. 4 illustrates an embodiment of Forward Osmosis Waste Heat Recovery System with Carbon Sequestration through the Production of Urea.

Example 4—Forward Osmosis Waste Heat Recovery System with Carbon Sequestration Through the Production of Urea Another specific embodiment of the instant invention is shown in FIG. 4. This example is similar to Example 3 except that saline water is used as the feed solution. Example 4 employs a similar heat recovery system that generates electricity and captures and sequesters $CO_2$ in the process described in Example 3, except desalinates water through forward osmosis. In this system, saline water and/or waste water is used as the feed solution and desalinated, purified water is produced as the remaining substance following the decomposition of aqueous ammonium carbonate, ammonium bicarbonate, ammonium carbamate or mixture thereof in the heat exchange process. This system allows for heat recovery through simultaneous and integrated/interconnected electricity generation, water desalination, carbon capture and sequestration and ammonium carbamate and other chemical synthesis.

Figure 5:
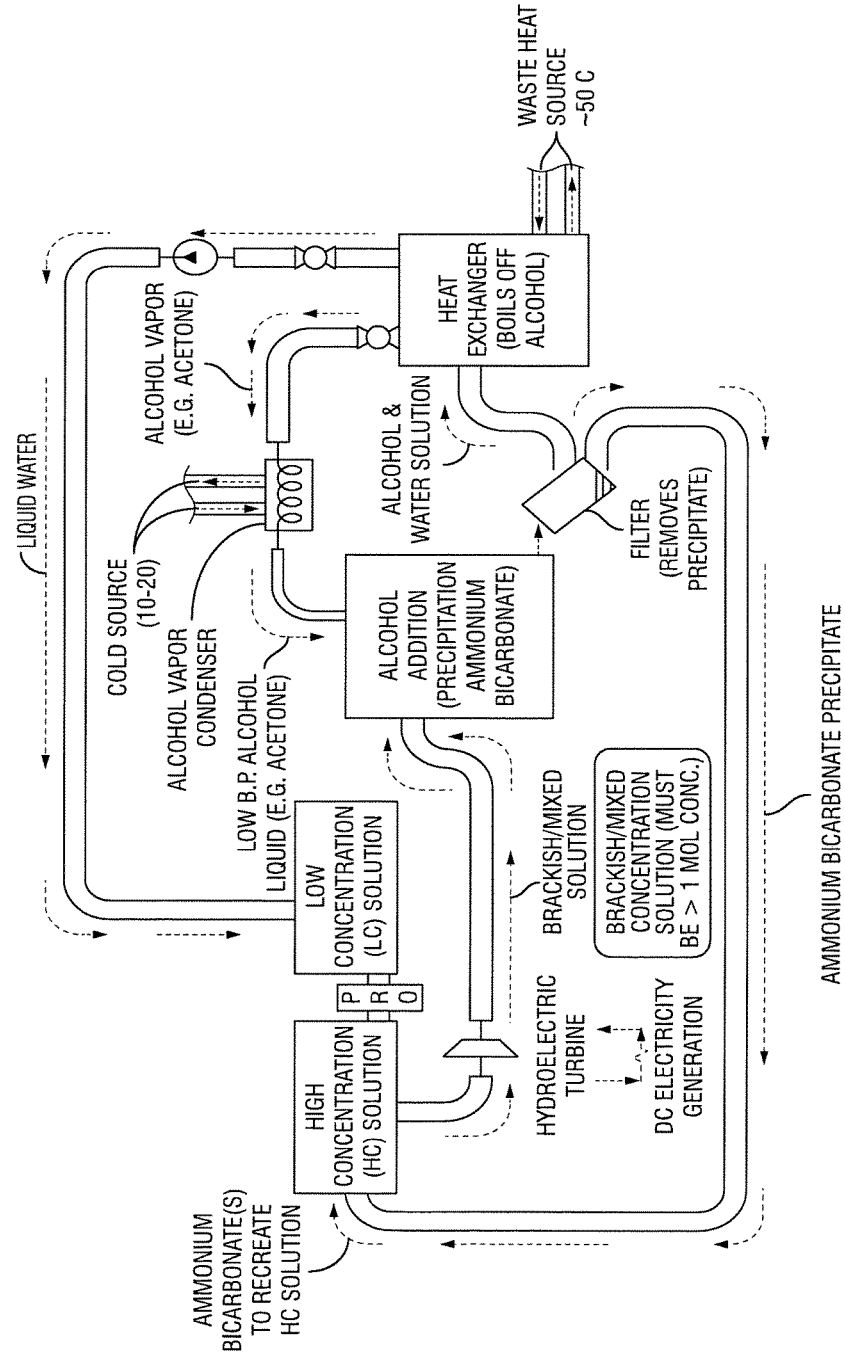
FIG. 5 illustrates an embodiment of Higher Efficiency Pressure Retarded Osmosis Waste Heat Recovery System through Addition of Water Soluble Organic Solvent to Precipitate Ammonium Bicarbonate Solid from Aqueous Solution.

Example 5—Higher Efficiency Pressure Retarded Osmosis Waste Heat Recovery System Through Addition of Water Soluble Organic Solvent to Precipitate Ammonium Bicarbonate Solid from Aqueous Solution Another specific embodiment of the instant invention is shown in FIG. 5. A heat recovery process that generates electricity from an engineered concentration gradient using the processes generally described in Example 1, except uses a novel method to reform the concentration gradient. The system engineers the concentration gradient through the addition of a water soluble solvent to the ammonium bicarbonate solution (generally >=1M aqueous ammonium bicarbonate concentration) to precipitate the ammonium bicarbonate as a solid. It is usually desirable that the solvent added is a non-azeotropic, water soluble, low boiling point substance, such as acetone or methyl formate. Other solvents may be effective that do not have some or all of the previously described properties, including, although not limited to isopropyl alcohol and ethanol, although may be less favorable depending upon the system specifics.

The ammonium bicarbonate precipitate is removed through a liquid-solid separation method, including, although not limited to filtration, the use of a centrifuge and other processes. The separated solid ammonium bicarbonate is transferred/recycled to concentrate the HC solution through dissolution. The organic solvent is removed from the water-solvent mixture remaining following precipitate separation process through fractional distillation or other method, removing the added solvent from the water. The water is used to replenish the low concentration feed solution, while the organic solvent vapor is condensed for reuse.

A gas turbine may be used to generate electricity from the gas expansion during the distillation process. The entire system allows for electricity production from waste heat through an Osmotic Heat Engine with a unique organic solvent ammonium bicarbonate precipitation system of engineering the concentration gradient that reduces energy consumption and improves energy efficiency. The system is generally most effective when the concentration of the diluted HC draw solution is >1M.

Figure 6:
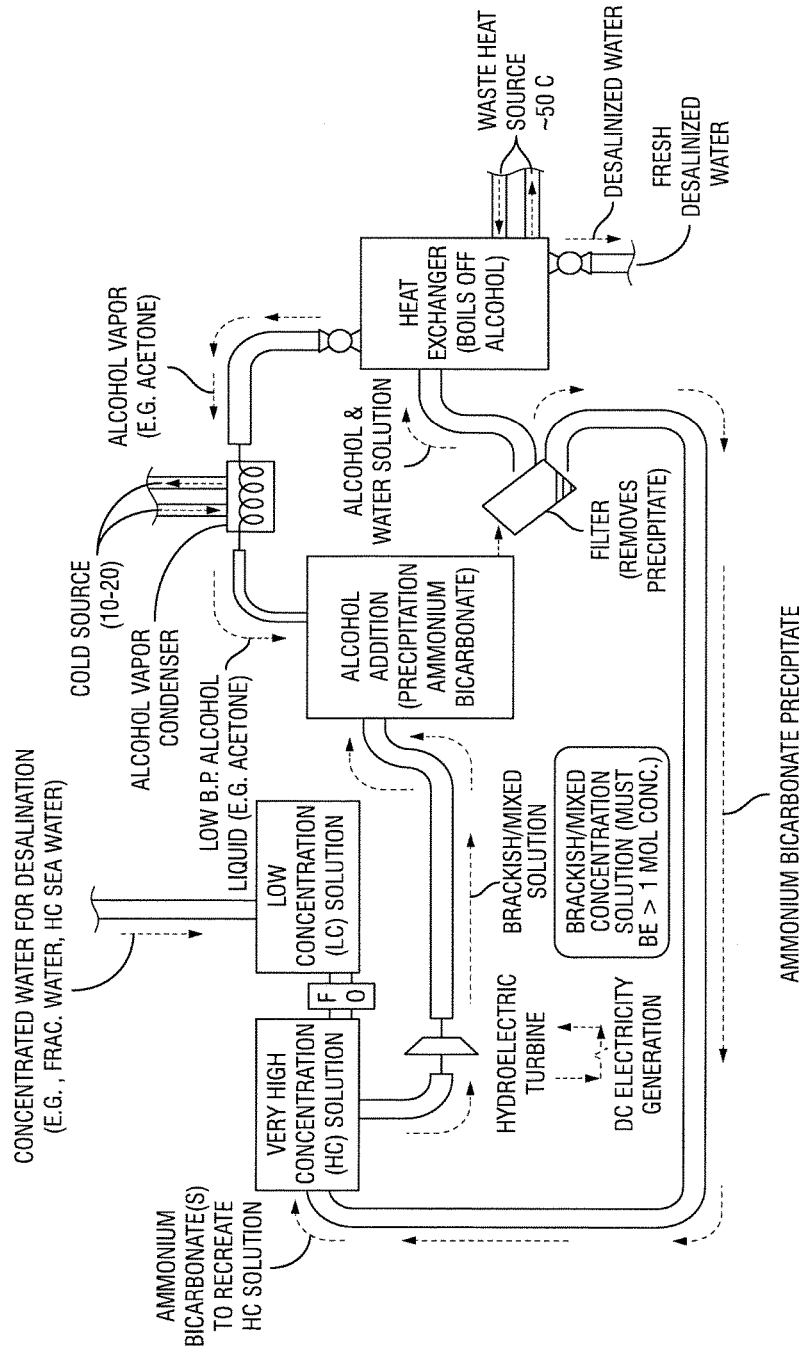
FIG. 6 illustrates an embodiment of Higher Efficiency Forward Osmosis High Concentration Water Desalination and Waste Heat Recovery System through Addition of Organic Solvent to Precipitate Ammonium Bicarbonate Solid from Aqueous Solution.

Example 6—Higher Efficiency Forward Osmosis High Concentration Water Desalination and Waste Heat Recovery System Through Addition of Organic Solvent to Precipitate Ammonium Bicarbonate Solid from Aqueous Solution Another specific embodiment of the instant invention is shown in FIG. 6. Example 6 is similar to Example 5 except uses saline water as the feed solution, converting the process into a forward osmosis water desalination system. The water soluble organic solvent addition system could significantly reduce the energy consumption and increase the efficiency of the desalination of very concentrated water.

A heat recovery system that utilizes the processes described in Example 5 for electricity generation, except uses saline water, including, although not limited to sea water, waste water or frac water, as the feed solution in a forward osmosis water desalination process. Fresh water is removed from the saline water feed solution via engineered osmosis through the creation of a concentration gradient in the presence of a semipermeable membrane. Purified, desalinated water is produced as a byproduct following the fractional distillation step, which removes the organic solvent from water using heat. The system is especially useful in desalinating very saline solutions because of its ability to convert the high concentration draw solution into pure water and solid ammonium bicarbonate with very little energy consumption.

Unlike current forward osmosis processes, which usually require decomposing all of the aqueous ammonium bicarbonate into its decomposition gases using low grade heat, this system's only energy consuming step involves boiling the proportionally minuscule amount of low boiling point organic solvent out of an aqueous solution during the distillation step, which requires significantly less energy. This system uses low grade heat to simultaneously generate electricity, while desalinating concentrated water at a greater efficiency than current forward osmosis processes.

Figure 7:
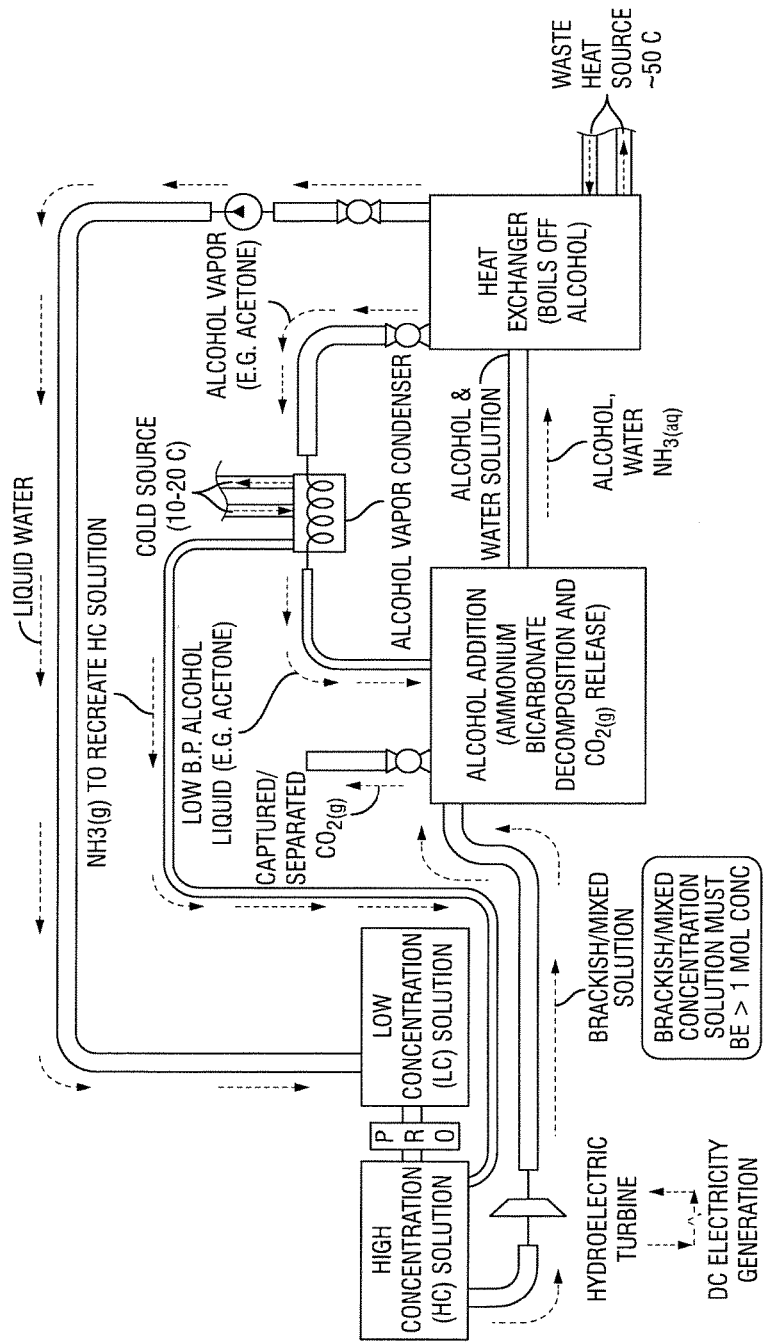
FIG. 7 illustrates an embodiment of Pressure Retarded Osmosis Waste Heat Recovery and Carbon Capture System through Addition of Water Soluble Organic Solvent to Decompose Ammonium Bicarbonate.

Example 7—Pressure Retarded Osmosis Waste Heat Recovery and Carbon Capture System Through Addition of Water Soluble Organic Solvent to Decompose Ammonium Bicarbonate Another specific embodiment of the instant invention is shown in FIG. 7. Example 7 is a low grade heat recovery system that generates electricity and captures carbon dioxide. The system utilizes the addition of a low boiling point organic solvent to a low concentration ammonium bicarbonate solution (<1M) to decompose the salt into $CO_{2(g)}$ and $NH_{3(aq)}$.

A heat recovery process that generates electricity from an engineered concentration gradient using the processes described in Example 1, except uses a novel method to reform the concentration gradient and capture carbon dioxide. When a highly water soluble organic solvent is added to a low concentration aqueous ammonium bicarbonate solution, the ammonium bicarbonate decomposes, releasing $CO_{2(g)}$, while $NH_{3(aq)}$ remains in the solution. This is different from the process described in Example 5 and 6, which involve the addition of an organic solvent to a higher concentration ammonium bicarbonate solution (>1M typically), which results in solid ammonium bicarbonate precipitating and not decomposing. When a water soluble organic solvent is added to a low concentration ammonium bicarbonate$_{(aq)}$ solution, the ammonium bicarbonate decomposes, while in a high concentration solution, the ammonium bicarbonate precipitates out as a solid. Example 7 uses the decomposition of a low concentration ammonium bicarbonate solution to reform the concentration gradient and capture carbon dioxide.

Following the Osmotic Heat Engine electricity generation process, a dilute ammonium bicarbonate solution is transferred to the water soluble organic solvent addition process. In this process, a water soluble organic solvent is added to the solution, resulting in the release of $CO_{2(g)}$ from the decomposition of ammonium bicarbonate. This $CO_{2(g)}$ can be bubbled through water to remove the organic solvent vapors due to vapor pressure and is then purified and captured. The $CO_{2(g)}$ can then sold, stored, used in enhanced oil recovery, or for any other use. Once the $CO_{2(g)}$ has left the original solution, the remaining solution, which is likely made up of water, the added organic solvent, a high concentration of $NH_3$, and a low concentration of $CO_{2(g)}$, is fractionally distilled to separate the organic solvent and $NH_3$ from the water. The water is used to replenish the LC feed solution, while the $NH_{3(g)}$ and the organic solvent vapors are separated by condensing the organic solvent, while the $NH_{3(g)}$ passes through. The $NH_{3(g)}$ is used to recreate the HC solution through reaction with $CO_{2(g)}$ from sources, including, although not limited to flue gas, and the organic solvent is recycled. To prevent the organic solvent vapor (resulting from vapor pressure) from contaminating the HC solution, the organic solvent+$NH_{3(g)}$ mixture can be bubbled through a low vapor pressure, nonpolar liquid which is less dense than the organic solvent at a liquid state. This nonpolar liquid will condense the organic solvent, allowing it to settle below the nonpolar liquid, while the $NH_{3(g)}$ bubbles through containing no organic solvent vapor.

Example 8—Integrated Process

This example is similar to Example 7 as it relates to an ammonium carbamate process. However, in Example 8 the process is integrated with a forward osmosis process, urea production, and/or a combination thereof in a similar fashion to the methods described in Example 1-4.

Example 9—Membrane Carbon Capture

Figure 8:
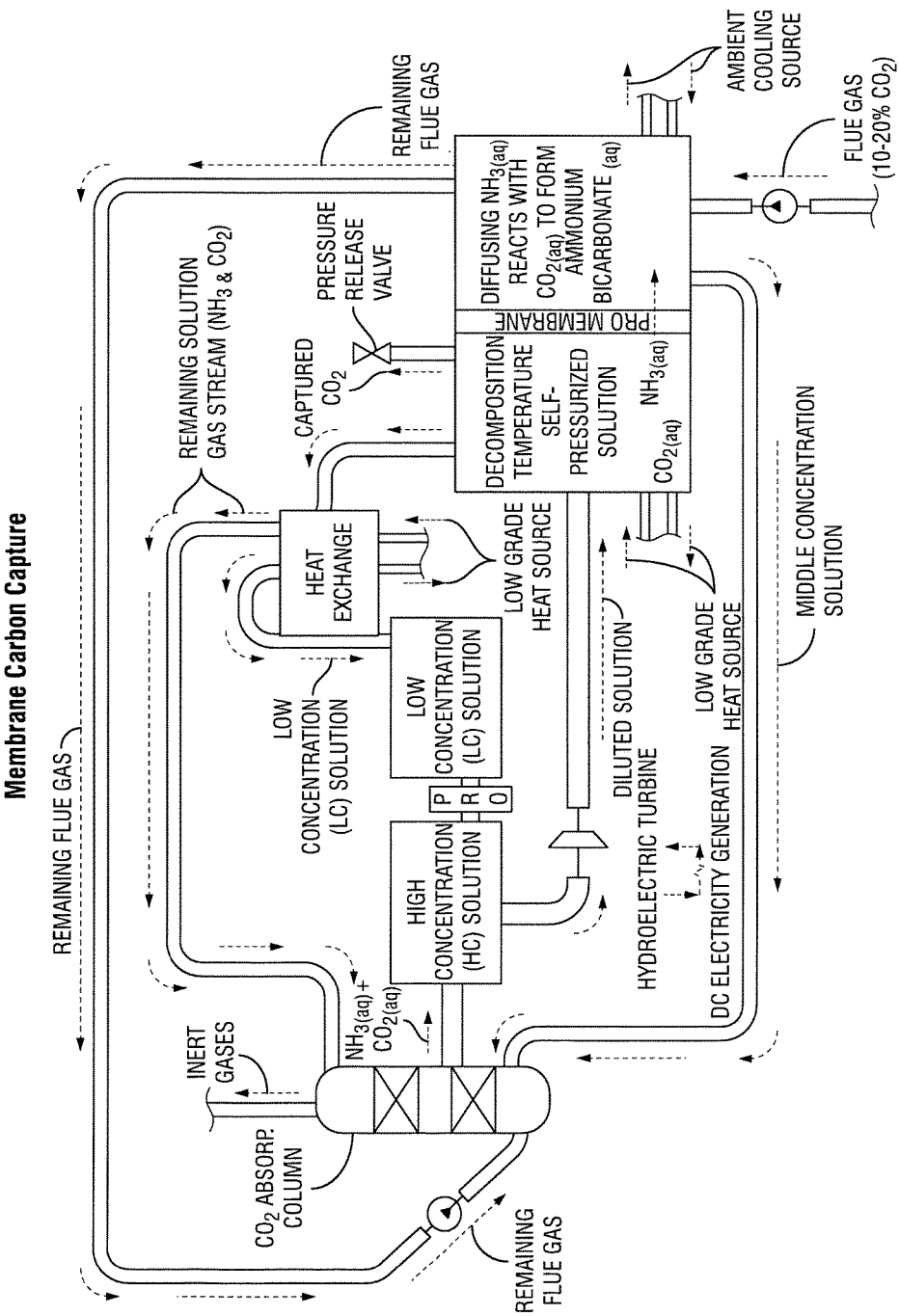
FIG. 8 illustrates an embodiment of Membrane Carbon Capture.

Another specific embodiment of the instant invention is shown in FIG. 8. In this continuous process example flue gas with from approximately about 10 to about 20 percent of carbon dioxide is captured with aqueous ammonia that is diffusing through a pressure retarded osmosis membrane and forms an aqueous solution of ammonium carbonate, ammonium bicarbonate, ammonium carbamate, or mixture thereof. The aqueous ammonia used is generated by heating the aqueous ammonium solution to its decomposition temperature. The remaining flue gas may then be routed to a carbon dioxide absorption column where additional carbon dioxide may be captured via contact with a middle concentrated solution and the resulting ammonium solution used as draw solution with a pressure retarded osmosis membrane to generate electricity and a dilute solution. The electricity generated may be sold or for other uses while the diluted solution may be recycled. Separated carbon dioxide gas generated may be employed in any useful process.

Example 10—Urea Production

Figure 9:
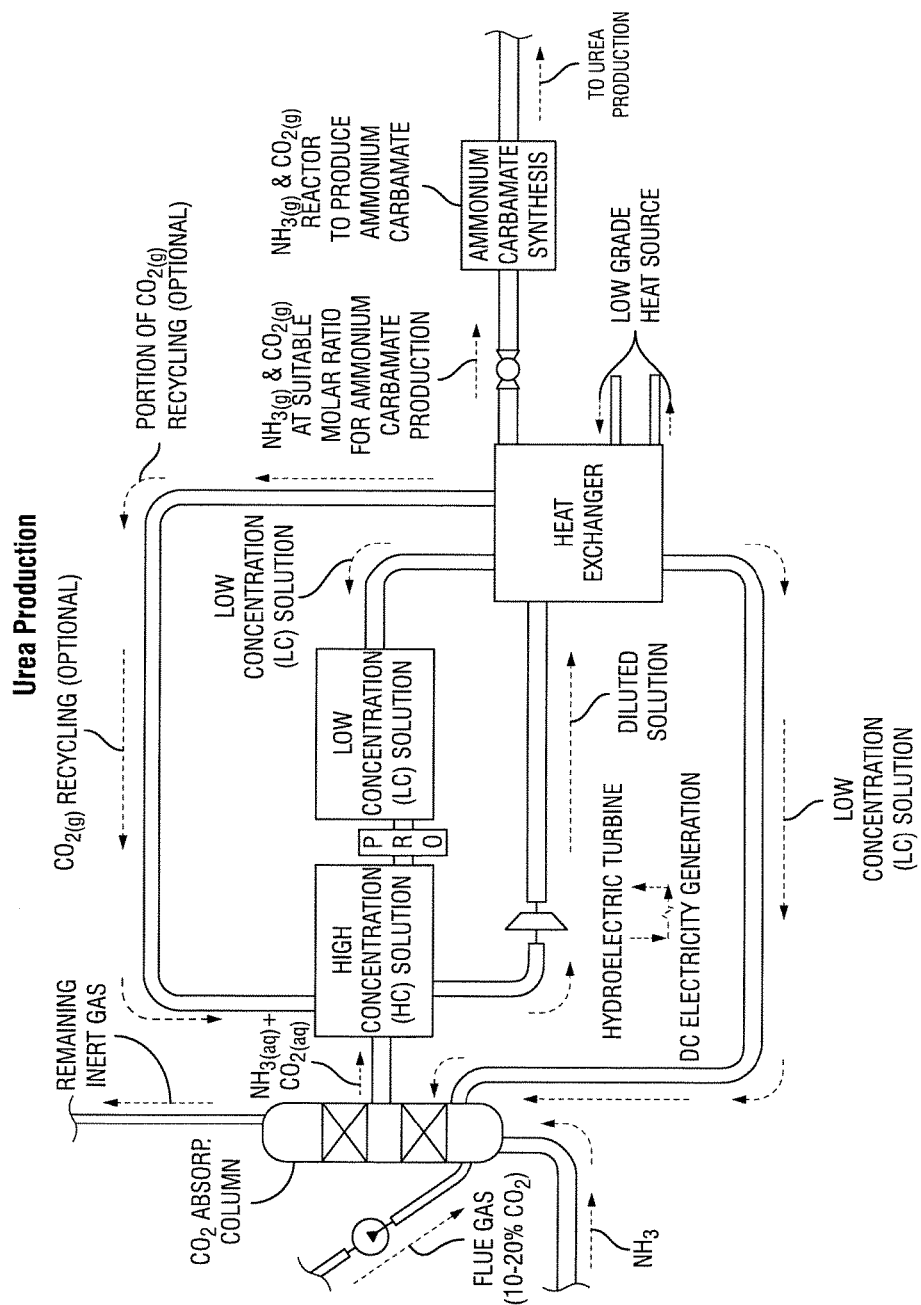
FIG. 9 illustrates an embodiment of Urea Production.

Another specific embodiment of the instant invention is shown in FIG. 9. This example is similar to that described above in Example 3 except that from the heat exchanger a portion of the carbon dioxide gas may be optionally recycled to the high concentration draw solution and the low concentration solution may be recycled to capture carbon dioxide from flue gas. Advantageously, in this example ammonia gas and carbon dioxide gas are generated at the heat exchanger in a suitable molar ratio for ammonium carbamate synthesis and conversion to urea.

Example 11—Urea Production Using Common Ion Precipitation

Figure 10:
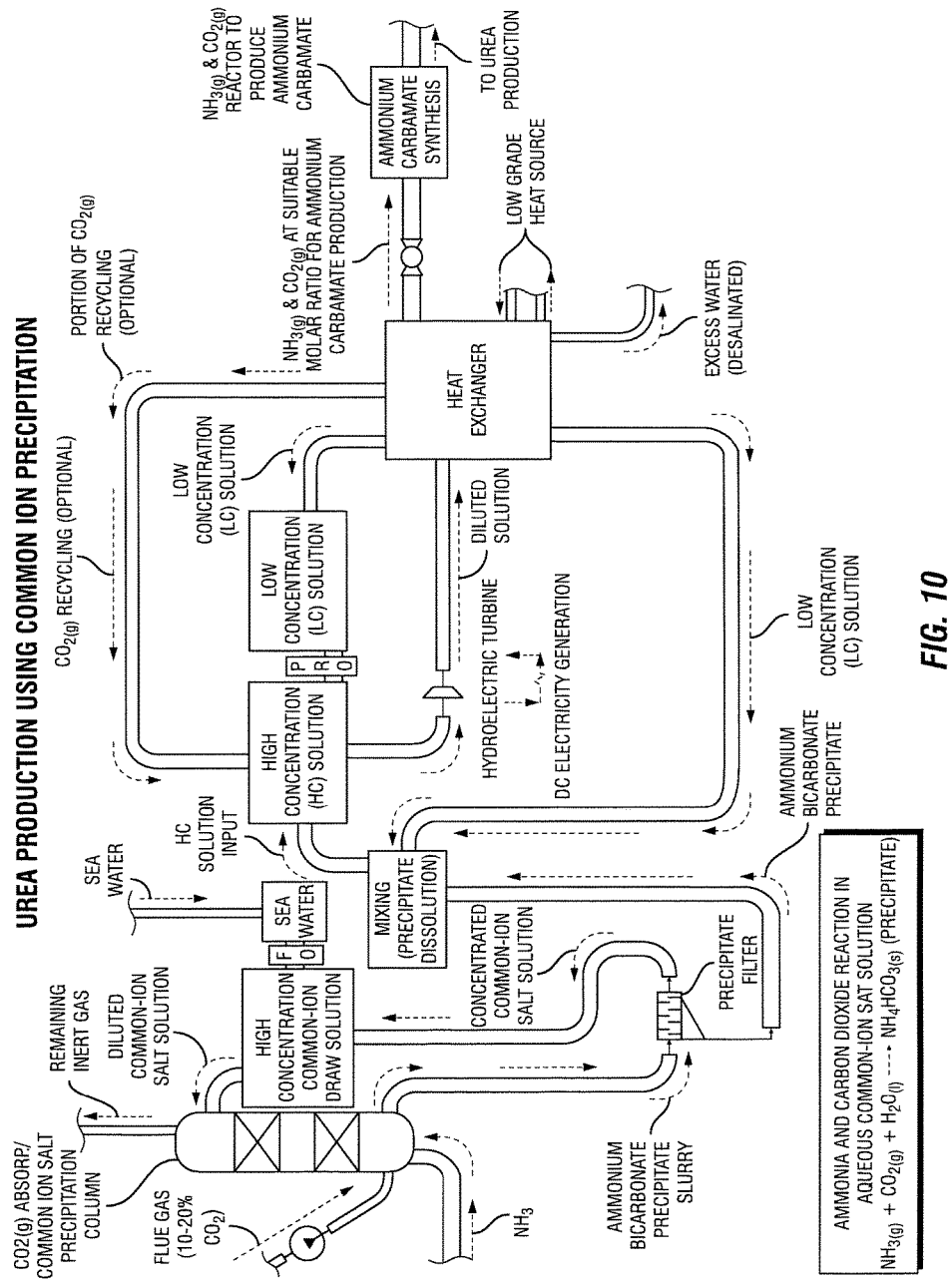
FIG. 10 illustrates an embodiment of Urea Production Using Common Ion Precipitation.

Another specific embodiment of the instant invention is shown in FIG. 10. This example is similar to that described above in Example 10 except that the high concentration draw solution is formed via a common ion precipitation method. In such a method ammonia gas, carbon dioxide gas and water react to form an ammonium bicarbonate precipitate. Specifically, flue gas and ammonia may react to form a high concentration common-ion draw solution that can be used as part of a continuous forward osmosis process as shown in the figure. Any precipitates formed can be mixed with a low concentrated solution to form the high concentration draw solution for the pressure retarded osmosis osmotic engine.

Example 12—Integrated Process and System for Simultaneous Heat Recovery, Carbon Capture/Sequestration, and Urea Production This example is an integrated process/system for simultaneous heat recovery, carbon capture/sequestration and urea production. The system comprises five components: 1) absorption of carbon dioxide; 2) electricity generation from concentration gradients; 3) solution decomposition; 4) ammonium carbamate production; and 5) urea production.

Component 1:

In the first component, there are two routes for absorbing carbon dioxide gas: 1) direct carbon dioxide gas absorption; 2) gas absorption by common-ion ammonium bicarbonate, carbonate salt precipitation. Either of these routes or even a combination can be employed.

1. Direct Carbon Dioxide Gas Absorption:

In the integrated process, regenerated low concentration (LC) or middle concentration (MC) solution is transferred into an absorption column. The solution will usually be either LC or de-ionized water when the decomposition step in the integrated process (Component 3) uses thermal decomposition with low grade heat under atmospheric pressure or ambient system pressure. When Component 3 is a semi-permeable membrane based carbon capture process, then the solution will usually be a middle concentration (e.g. from about 0.05 to about 1M ammonium bicarbonate solution).

Ammonia gas is released into the absorption column where it is absorbed by the LC or MC solution to form an aqueous ammonia solution. When ammonia is absorbed by LC solution, the solution will typically be aqueous ammonia. When ammonia is absorbed by MC solution, the solution will typically be aqueous ammonia:carbon dioxide species at an $NH_3:CO_2$ molar ratio of from about 1:1 to about 10:1.

A gas stream containing carbon dioxide (e.g. flue gas, methane reforming gas) is released into the absorption column, where it reacts with the aqueous ammonia to form an aqueous ammonium-carbonate, bicarbonate, carbamate solution. The remaining inert gases ($N_{2(g)}$, $O_{2(g)}$) may be released back into the atmosphere. In room temperature pressure (RTP) conditions, flue gas $CO_2$ absorption will form a solution at an $NH_3:CO_2$ molar ratio of ~3:1. This is described in, for example, Bai et al., *Ind. Eng. Chem. Res.*, 1997, 36 (6), pp 2490-2493 incorporated herein by reference.

The <1.5:1 $NH_3:CO_2$ molar ratio used for Pressure Retarded Osmosis (PRO) membranes (Component 2) can be achieved by reducing the temperatures in the absorption column (cooling via heat sink, such as ocean, lake or river water) and/or recycling a portion of the carbon dioxide gas released in the solution decomposition (Component 3) to form a higher partial pressure of carbon dioxide gas after the flue gas carbon dioxide absorption, increasing the proportional amount of $CO_2$ in solution. Carbon dioxide in methane reforming gases following the low temperature gas-shift is at a significantly higher partial pressure (~2.98 bar, 16 bar total pressure as described by Molberg et al. "Hydrogen from Steam-Methane Reforming with $CO_2$ Capture" 20th Annual International Pittsburgh Coal Conference Sep. 15-19, 2003 Pittsburgh, Pa. incorporated herein by reference) and, due to this higher solubility of carbon dioxide, will not require $CO_2$ recycling.

2. Common-Ion Ammonium Bicarbonate, Carbonate Salt Precipitation:

In a separate osmotic heat engine or forward osmosis (FO) component, a salt solution containing a common ion, such as ammonium, carbonate, bicarbonate, carbamate, is employed as a draw solution. Such solutions include, for example, ammonium sulfate, ammonium nitrate, potassium carbonate, or potassium bicarbonate. In this manner the presence of the common ion salt with a more soluble common ion will cause the lower solubility ammonium bicarbonate to precipitate.

Once the draw solution becomes diluted during the PRO or FO, the solution is sent into the absorption column.

Ammonia and carbon dioxide are bubbled, sparged, or otherwise transferred through this aqueous solution so as to react and form ammonium bicarbonate, ammonium carbonate, or a mixture thereof. Due to the common-ion effect from the presence of the ammonium sulfate, ammonium nitrate, potassium bicarbonate or potassium carbonate, the solubility of the solution of ammonium bicarbonate, ammonium carbonate or mixture is significantly less than in a pure aqueous solution. This causes the salt comprising ammonium bicarbonate, ammonium carbonate or mixture to more readily precipitate out of solution.

The salt of ammonium bicarbonate, ammonium carbonate or mixture precipitates with the removal of a water via the following reactions:

$$NH_{3(aq)}+CO_{2(aq)}+H_2O_{(l)} \rightarrow NH_4HCO_{3(s)}; \quad 1)$$

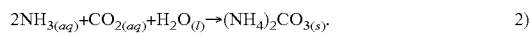

$$2NH_{3(aq)}+CO_{2(aq)}+H_2O_{(l)} \rightarrow (NH_4)_2CO_{3(s)}. \quad 2)$$

The precipitate may be filtered continuously from the common-ion salt solution and transferred to an ammonium carbonate, ammonium bicarbonate osmotic engine, where it can be dissolved in regenerated LC or MC solutions to form the draw solution for the process. Additionally or alternatively, the precipitate can also be sent directly to Component 3, where it may be decomposed with low grade heat into $NH_{3(g)}$ and $CO_{2(g)}$ (which are reacted to form ammonium carbamate) and pure $H_2O_{(l)}$. Over time enough water may be removed by the salt precipitation of ammonium carbonate, ammonium bicarbonate or mixture that the common-ion salt solution becomes sufficiently concentrated to be recycled as a draw solution.

Component 2:

The electricity generation component (Component 2), if included, can be conducted via three main methods or it can be absent from the process. In the instance where it is absent from the process, the solution formed in Component 1 is typically transferred directly to Component 3, where the solution is decomposed.

Figure 12:
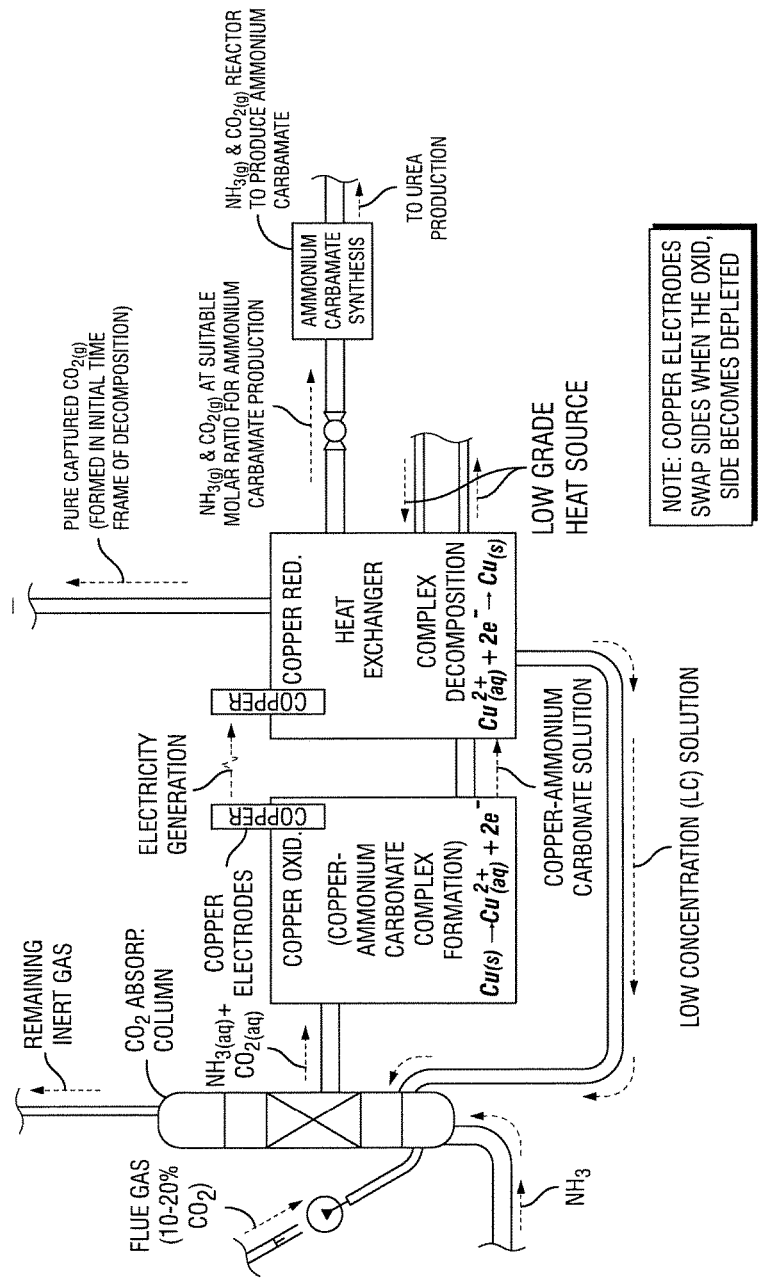
FIG. 12 illustrates an embodiment of Basic Production Process with Copper Battery.

1. Electricity Generation Using Pressure Retarded Osmosis (PRO):

The <1.5:1 $NH_3:CO_2$ molar ratio solution created in Component 1 is used as a draw solution. As shown in FIG. 12 at an $NH_3:CO_2$ molar ratio of 1.5:1, the solution has a pH of ~>8.5 at a temperature of 298K. PRO is most effective when ionic NH4+ species are present. $NH_{3(aq)}$ (non-ionic species) acts in a similar manner to water with PRO membranes. The LC or de-ionized solution regenerated in the integrated process is used as a feed solution. Separating the draw and feed solutions is a PRO membrane, a thin-film composite (TFC) membrane made up of a selective polyamide and a polysulfone support layer. Suitable membranes are described in, for example, Yip et al., *Environ. Sci. Technol.*, 2011, 45 (10), pp 4360-4369 which is incorporated herein by reference.

Water moves from the LC feed solution to the draw solution due to the natural force of osmosis generated from the difference in osmotic pressure between the two solutions. The flow of water across the membrane is fed into a hydroelectric turbine to generate electricity. The solution remaining after the hydroelectric turbine is a diluted version of the initial draw solution. This solution is transferred to Component 3 to decompose the solute and regenerate the LC or MC solutions.

2. Further Electricity Generation Through Employing a Copper-Ammonium Carbonate, Bicarbonate Redox Battery Following PRO (FIG. 11):

The diluted ammonia-carbon dioxide draw solution produced after PRO is transferred into a solution in contact with a copper electrode (can also be, for example, Zinc, Nickel, Silver, Lead, Cobalt). The ammonia species reacts (oxidation) with the copper electrode (anode) to form a water soluble complex cation. The solution is then transferred to the heat exchanger in Component 3 (either in a continuous or in a batch system), where another copper electrode (cathode) is present in solution. The solution is decomposed using low grade heat in the heat exchanger, causing solid copper ($Cu_{(s)}$) to be deposited on the copper electrode/cathode (reduction). As the copper electrode in the complex ion formation solution is oxidized and the copper electrode in the heat exchange is reduced, DC electricity is generated by connecting the electrodes with, for example, wire, thereby forming a complete circuit. The electrodes may be periodically swapped between solutions to ensure the copper electrode in the oxidation solution does not become too depleted.

Figure 11:
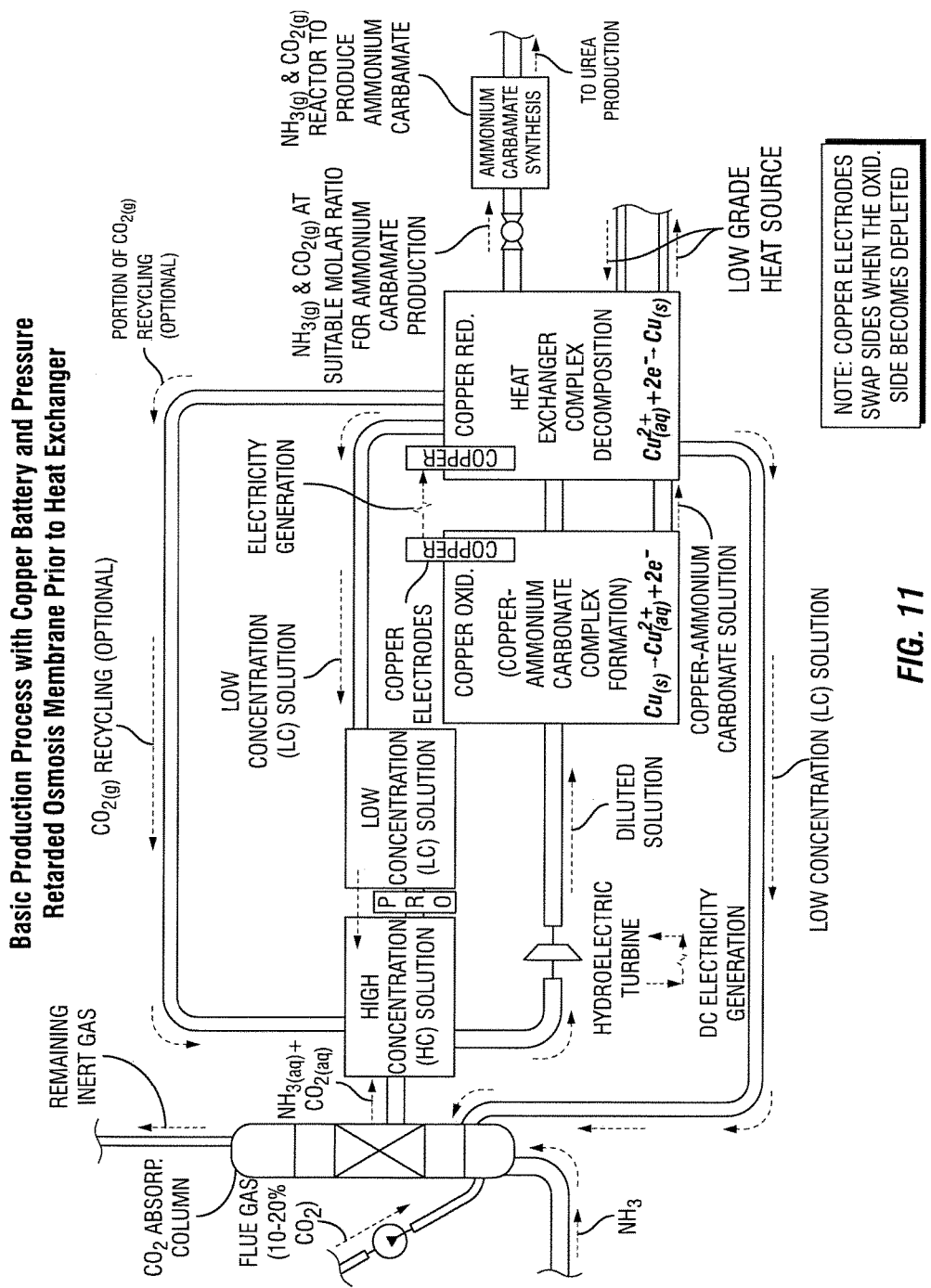
FIG. 11 illustrates an embodiment of Basic Production Process with Copper Battery and Pressure Retarded Osmosis Membrane Prior to Heat Exchanger.

FIG. 11 depicts a diagram of the system wherein a novel regenerated copper-ammonium carbonate, bicarbonate battery is employed to generate additional electricity in the process. Copper is oxidized in the complex-ion formation solution and is reduced in the thermal decomposition solution (heat exchange), generating DC electricity. Copper solid is removed/depleted from the copper electrode in the Copper Oxidation solution and deposited on the copper electrode in the Copper Reduction solution. The electrodes may be switched between solutions periodically to ensure the copper electrode in the oxidation solution never becomes too depleted.

3. Electricity Generation from Employing a Copper-Ammonium Carbonate, Bicarbonate Redox Battery (Membrane-Free Process) (FIG. 12):

The ammonia-carbon dioxide solution produced in component 1 is transferred into a solution in contact with a copper electrode (can also be, for example, Zinc, Nickel, Silver, Lead, Cobalt). The ammonia species reacts (oxidation) with the copper electrode (anode) to form a water soluble complex cation. The solution is transferred to the heat exchanger in Component 3 (either in a continuous or in a batch system), where another copper electrode (cathode) is present in solution. The solution is decomposed using low grade heat in the heat exchanger, causing solid copper ($Cu_{(s)}$) to be deposited on the copper electrode/cathode (reduction). As the copper electrode in the complex ion formation solution is oxidized and the copper electrode in the heat exchange is reduced, DC electricity is generated by connecting the electrodes with wire, forming a complete circuit. The electrodes may be periodically swapped between solutions to ensure the copper electrode in the oxidation solution never becomes too depleted.

FIG. 12 depicts a diagram of the system wherein a membrane-less variation of the system in FIG. 11 generates electricity and valuable nitrogen compounds. This variation of the system generates electricity with a regenerated copper-ammonium carbonate, bicarbonate battery, while advantageously continuing to produce an ammonia-carbon dioxide gas mixture at a suitable molar ratio for ammonium carbamate synthesis.

4. Further Electricity Generation Through Employing a Copper-Ammonium Carbonate, Bicarbonate Redox Battery Prior to PRO (FIG. 13).

Figure 13:
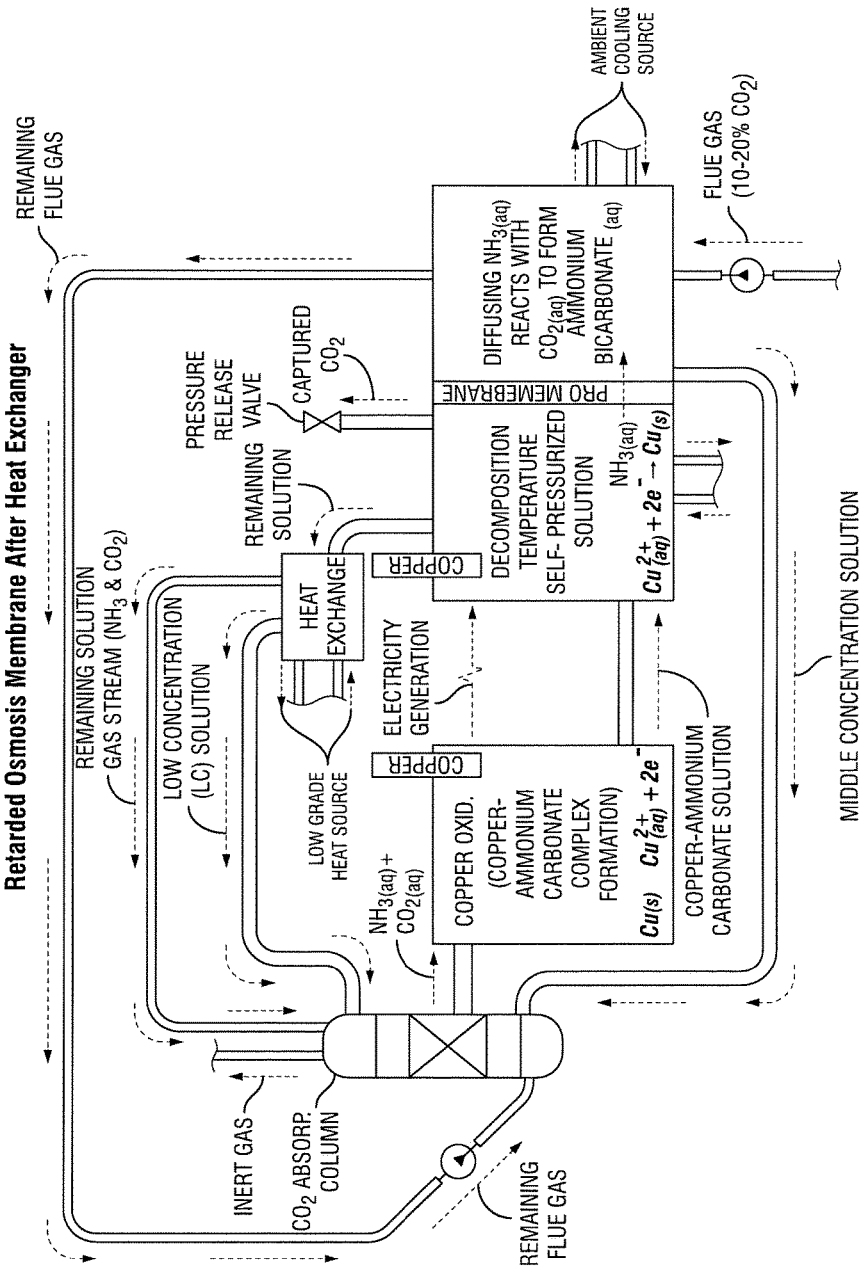
FIG. 13 illustrates an embodiment of Basic Production Process with Copper Battery and Pressure Retarded Osmosis Membrane After Heat Exchanger.

FIG. 13 depicts a variation of the above systems that generates electricity and captures carbon dioxide. This variation of the system generates electricity with a regenerated copper-ammonium carbonate, bicarbonate battery, while capturing carbon dioxide using an aqueous semipermeable membrane.

PRO Effectiveness

Figure 14:
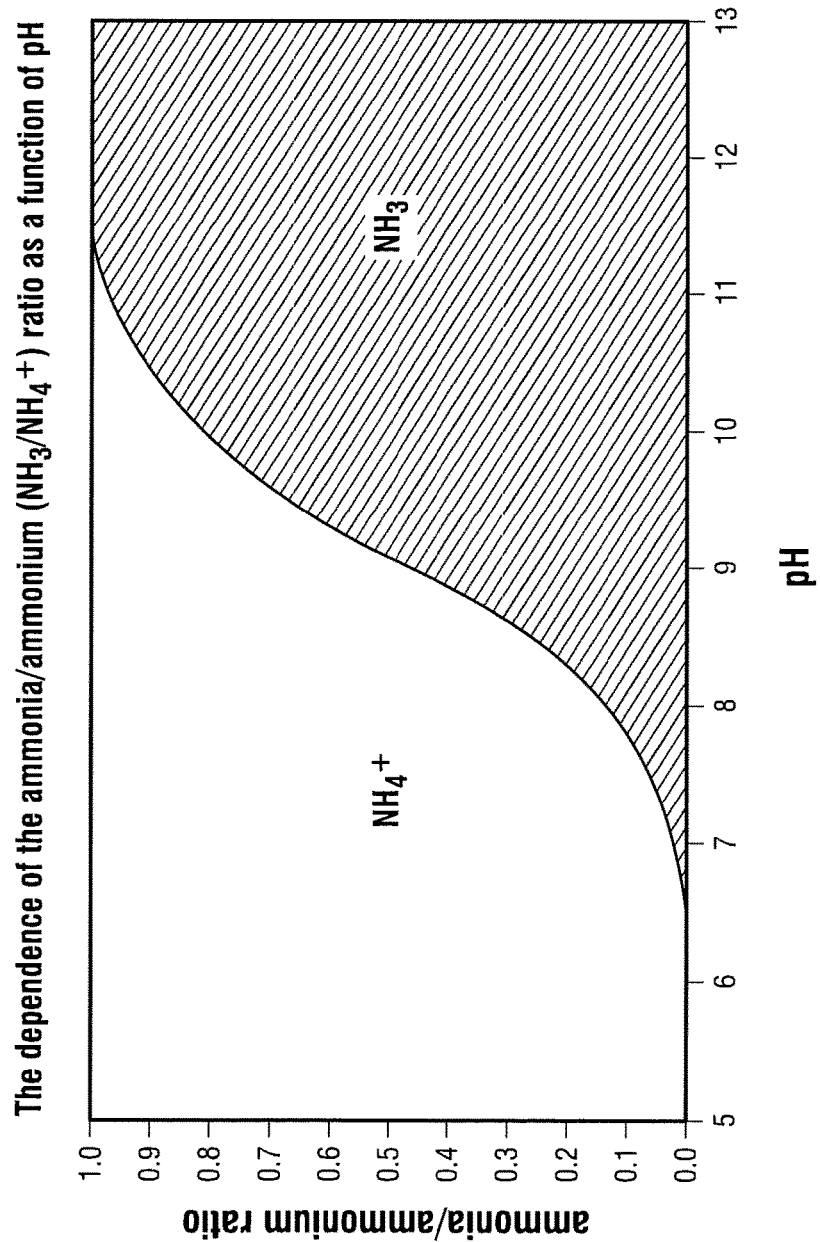
FIG. 14 illustrates the dependence of ammonia/ammonium ion ratio as a function of pH.

As shown in FIG. 14, at an $NH_3:CO_2$ molar ratio of 1.5:1, the solution has a pH of about 9 at a temperature of 298K. Pressure retarded osmosis is generally effective when NH4+ species are present. $NH_{3(aq)}$ (non-ionic species) often acts in a similar manner to water with most PRO membranes.

5. Electricity Generation Using Reverse Electro Dialysis (RED):

The ammonia-carbon dioxide species solution created in component 1 is used as a concentrated solution while the LC or de-ionized water solution regenerated in the integrated process is used as the opposing solution. The solutions are separated by stacked anion and cation exchange membranes (AEM and CEM). On the ends of the stack, there is an anode and a cathode. Electricity is generated when the net negative change produced by the AEM and the net positive charge produced by the CEM is neutralized by the anode and cathode in a DC circuit. Such methods are described in, for example, Paripati et al., US 20140026567 which is incorporated herein by reference.

6. Other Methods to Generate Electricity from Aqueous Concentration Gradients (e.g. CAPMIX):

There are other methods for generating electricity from concentration gradients, including capacitive mixing power production (CAPMIX). These methods include the use of Nano-Battery Electrodes (NBE), Capacitive Double Layer Expansion (CDLE), and/or Capacitors Charged by the Donnan Potentials (CDP). These methods are described in, for example, *Energy Procedia*, Volume 20, 2012, Pages 108-115 Technoport 2012—Sharing Possibilities and 2nd Renewable Energy Research Conference (RERC2012) CAPMIX—Deploying Capacitors for Salt Gradient Power Extraction; M. F. M. Bijmans, et al. which is incorporated herein by reference.

Component 3:

Involves the decomposition of the solution created in Component 2 or the precipitate formed in Component 1 in any convenient manner such as one of the four described below or a combination thereof.

1. Low Grade Temperature Thermal Decomposition Under System Pressure Conditions:

The diluted solution created in Component 2 or the precipitate created in Component 1 may be decomposed into ammonia and carbon dioxide gases at the decomposition temperature of the ammonium carbonate, ammonium bicarbonate or mixture at a system pressure of from about 0.75 to 1.25 atm. The decomposition of the ammonium carbonate, ammonium bicarbonate or mixture solution involves the initial release of carbon dioxide gas, with substantially less ammonia gas being released. A portion of this higher partial pressure carbon dioxide gas stream can be recycled back to Component 1 and/or Component 2 to generate a solution with an $NH_3:CO_2$ molar ratio <1.5:1 for PRO energy generation. This gas stream can also be condensed via compression and/or cryogenic cooling to produce substantially separated liquid ammonia and carbon dioxide gas with in some cases a small quantity of ammonium carbamate precipitate. Over time, a higher partial pressure of ammonia gas begins to release from solution, at which point the gas mixture created can be transferred to Component 4 for ammonium carbamate production. Advantageously, this process requires less work energy than current carbon capture processes, including the chilled ammonia process, due to the lack of a higher pressure and temperature (80-110 C) equilibrium, which is required in these carbon capture processes as described by Yeh, J., & Pennline, H. (2004), Absorption and regeneration studies for $CO_2$ capture by aqueous ammonia, *Third Annual Conference on Carbon Capture & Sequestration*. This equilibrium is not required in this route because the gas stream produced is an ammonia and carbon dioxide gas mixture at a suitable molar ratio for ammonium carbamate/urea production, not pure carbon dioxide gas.

2. Using Aqueous Semi-Permeable (e.g. PRO) Membrane Under Low Grade Temperatures to Separate Ammonia and Carbon Dioxide:

This route significantly reduces the energy consumption involved with carbon capture by reducing the need to thermally convert ammonia from its aqueous species to a gaseous species (very energy intensive process). Additionally, it leaves aqueous carbon dioxide in solution without an accompanying Ammonia species (i.e. $NH_3:CO_2$ molar ratio <1:1), causing pure Carbon Dioxide to come out of the solution readily under RTP conditions.

The solution created in Component 2 is transferred into a closed chamber where it is in contact with a semi-permeable membrane, such as the PRO membrane described in Component 2. This solution is heated to the decomposition temperature of the solute of ammonium carbonate, ammonium bicarbonate or mixture, although the constituents of the solute do not come out of the solution as gases because of the closed chamber. Instead, the ammonia and carbon dioxide stay in solution as $NH_{3(aq)}$ and $CO_{2(aq)}$ species (non-ionic forms). On the other side of the semi-permeable membrane is cooled dilute carbonic acid solution (e.g. 10° C.) sparged with flue gas containing carbon dioxide (of which a small portion dissolves, forming the dilute carbonic acid, or $CO_{2(aq)}$ solution). The semipermeable membrane rejects the $CO_{2(aq)}$ species from diffusing because of its larger molecule size and dissimilar properties to that of water, while the $NH_{3(aq)}$ species (having similar molar mass and properties to that of water) is not rejected by the membrane (attribute of PRO membranes). The $NH_{3(aq)}$ diffuses across the membrane into the dilute carbonic acid solution, where it reacts to form aqueous ammonium carbonate or ammonium bicarbonate. Eventually, the solution that forms in this reaction is transferred to Component 1 as a middle concentration (MC) solution. A valve is opened above the solution on the opposing side of the semi-permeable membrane (now containing more $CO_{2(aq)}$ than $NH_{3(aq)}$ species due to the diffusion of $NH_{3(aq)}$ species across the semipermeable membrane), causing the solution to depressurize. Carbon dioxide gas comes out of solution under RTP/ambient conditions and is pure for use. This depressurization will likely cause a rapid drop in temperature of the solution, which has application in cooling, including cooling Component 1 to increase the rate of absorption. The remaining solution after the $CO_{2(g)}$ has been released is heated using low grade heat to remove and recycle any remaining $NH_{3(aq)}$ species and is transferred to Component 2 as an LC solution.

3. Water Soluble Solvent Carbon Dioxide and Ammonia Separation:

Following Component 2, a dilute ammonium bicarbonate solution is transferred to the water soluble organic solvent addition process. In this process, a water soluble organic solvent is added to the solution, resulting in the release of $CO_{2(g)}$ from the decomposition of ammonium bicarbonate. This $CO_{2(g)}$ can be bubbled through water to remove the organic solvent vapors due to vapor pressure and is then purified and captured. The $CO_{2(g)}$ can then sold, stored, used in enhanced oil recovery, or for any other use. Once the $CO_{2(g)}$ has left the original solution, the remaining solution, which is likely made up of water, the added organic solvent, a high concentration of $NH_3$, and a low concentration of $CO_{2(g)}$, is fractionally distilled or uses membrane distillation (MD) to separate the organic solvent and $NH_3$ from the water. The water is used to replenish the LC feed solution, while the $NH_{3(g)}$ and the organic solvent vapors are separated by condensing the organic solvent, while the $NH_{3(g)}$ passes through. The $NH_{3(g)}$ is used to recreate the HC solution through reaction with $CO_{2(g)}$ from sources, including, although not limited to flue gas, and the organic solvent is recycled. To prevent the organic solvent vapor (resulting from vapor pressure) from contaminating the HC solution, the organic solvent+$NH_{3(g)}$ mixture can be bubbled through a low vapor pressure, nonpolar liquid which is less dense than the organic solvent at a liquid state. This nonpolar liquid will condense the organic solvent, allowing it to settle below the nonpolar liquid, while the $NH_{3(g)}$ bubbles through containing no organic solvent vapor.

4. Water-Soluble Organic Solvent Ammonium Bicarbonate, Carbonate, Mixture Thereof Precipitation:

The system engineers the concentration gradient through the addition of a water soluble solvent to the ammonium carbonate, bicarbonate mixture solution (generally >=1M aqueous ammonium bicarbonate concentration) to precipitate the ammonium bicarbonate as a solid. It is usually desirable that the solvent added is a non-azeotropic, water soluble, low boiling point substance, such as acetone or methyl formate. Other solvents may be effective that do not have some or all of the previously described properties, including, although not limited to isopropyl alcohol and ethanol, although may be less favorable depending upon the system specifics.

The ammonium bicarbonate precipitate is removed through a liquid-solid separation method, including, although not limited to filtration, the use of a centrifuge and other processes. The separated solid ammonium bicarbonate is transferred/recycled to concentrate the HC solution through dissolution. The organic solvent is removed from the water-solvent mixture remaining following precipitate separation process through fractional distillation or other method, removing the added solvent from the water. The water is used to replenish the low concentration feed solution, while the organic solvent vapor is condensed for reuse.

A gas turbine may be used to generate electricity from the gas expansion during the distillation process. The entire system allows for electricity production from waste heat through an osmotic heat engine with a unique organic solvent ammonium bicarbonate precipitation system of engineering the concentration gradient that reduces energy consumption and improves energy efficiency. The system is generally most effective when the concentration of the diluted HC draw solution is >1M. The system can also be used for lower work energy consumption desalination by using saline water as a feed solution and forward osmosis semipermeable membrane instead of a PRO membrane.

Component 4:

This component generally involves reacting the ammonia and carbon dioxide gases generated in Component 3 to produce ammonium carbamate, an essential precursor/intermediate in urea production. Ammonium carbamate production processes currently used in urea production plants are employed in this component. Advantageously, Component 3 may produce the $NH_{3(g)}$ and $CO_{2(g)}$ at the appropriate molar ratio for the specific ammonium carbamate synthesis process being employed. Current methods include contacting the gases directly in a gas compression system. Processes for producing ammonium carbamate include sparging the $NH_{3(g)}$ and $CO_{2(g)}$ into an organic solvent at a 1-2:1 $NH_3$:$CO_2$ molar ratio in a continuous flow reactor as described in, for example, Barzakli et al., *Green Chem.*, 2011, 13, 1267-1274 which is incorporated herein by reference. Other compounds may be added to the gas stream or solutions. For example, methanol, may be added as it can be reacted with ammonia to form methylamine, dimethylamine and trimethylamine, with potential application in pesticides and pharmaceuticals. Such trimethylamine also may potentially be used as draw solutions as described in, for example, Boo et al., *Journal of Membrane Science*, Volume 473, 1 Jan. 2015, Pages 302-309 which is incorporated by reference herein.

Component 5:

Component 5 produces urea from ammonium carbamate (produced in Component 4) or from ammonia and carbon dioxide gas mixtures. Such processes may be conducted in any useful manner but advantageously the molar ratios of the substances produced in the present invention are particularly useful for Component 5.

The claimed subject matter is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A process for separating carbon dioxide comprising:
   forming a first solution comprising a salt of carbonate, bicarbonate, carbamate, or a mixture thereof; and
   decomposing the first solution to form a second aqueous solution comprising ammonia, amine, carbon dioxide, or a mixture thereof;
   wherein the decomposing of the first solution to form said second aqueous solution is conducted in the presence of a water-soluble organic solvent to form gaseous carbon dioxide in the absence of precipitate; and then
   separating at least a portion of the solvent from the second aqueous solution.

2. The process of claim 1 wherein the first and second solution each comprise aqueous ammonia, amine, or both.

3. The process of claim 1 wherein the decomposing of the first solution occurs in the absence of high pressure.

4. The process of claim 1 wherein the decomposing of the first solution further uses a pump, vacuum pump, or other device.

5. The process of claim 1 which further comprises compressing the formed gaseous carbon dioxide.

6. The process of claim 1 which further comprises bubbling the formed gaseous carbon dioxide through water to remove soluble vapor.

7. The process of claim 1 which further comprises bubbling the formed gaseous carbon dioxide through water to remove organic solvent vapor, ammonia gas, or both.

8. The process of claim 1 which further comprises removing organic solvent vapor from the formed gaseous carbon dioxide.

9. The process of claim 1 which comprises first capturing carbon dioxide from a gas stream to produce the first solution and wherein said gas stream comprises flue gas.

10. The process of claim 1 which comprises first capturing carbon dioxide from a gas stream to produce the first solution and wherein said gas stream comprises a steam methane reforming gas.

11. The process of claim 1 which comprises first capturing carbon dioxide from a gas stream to produce the first solution and wherein said gas stream comprises a low temperature gas shift gas.

12. The process of claim 1 which comprises first capturing carbon dioxide from a gas stream to produce the first solution and wherein said capturing is conducted at a temperature such that a substantial portion of the ammonia is condensed.

13. The process of claim 1 which comprises first capturing carbon dioxide from a gas stream to produce the first solution and wherein said capturing is conducted at a reduced temperature using a heat sink.

14. The process of claim 13 wherein the heat sink comprises water.

15. The process of claim 1 which comprises first capturing carbon dioxide from a gas stream to produce the first solution and wherein said capturing is conducted at a reduced temperature using an absorption column.

16. The process of claim 1 which comprises first capturing carbon dioxide from a gas stream to produce the first solution and wherein said capturing is conducted at a reduced temperature using an absorption column with a heat sink.

17. The process of claim 16 wherein the heat sink comprises water.

18. The process of claim 1 which comprises first capturing carbon dioxide from a gas stream to produce the first solution and wherein said gas stream is subjected to a purification step subsequent to said capturing of carbon dioxide.

19. The process of claim 18 wherein said purification step captures additional carbon dioxide.

20. The process of claim 1 wherein the decomposing of the solution occurs at a temperature less than 80° C.

* * * * *